United States Patent [19]

Edwards et al.

[11] Patent Number: 5,164,371
[45] Date of Patent: Nov. 17, 1992

[54] HETEROCYCLIC KETONES

[75] Inventors: Philip D. Edwards, Claymont, Del.;
Joseph J. Lewis, West Chester, Pa.;
Charles W. Perkins, Wilmington,
Del.; Diane A. Trainor, Glen Mills;
Richard A. Wildonger, Morgan
Hollow, both of Pa.

[73] Assignee: ICI Americas Inc., Wilmington, Del.

[21] Appl. No.: 193,317

[22] Filed: May 11, 1988

[30] Foreign Application Priority Data

May 11, 1987 [GB] United Kingdom ................ 8711050
Feb. 11, 1988 [GB] United Kingdom ................ 8803206

[51] Int. Cl.$^5$ ................ C07D 237/08; C07D 239/06;
C07K 5/08; A61K 37/02
[52] U.S. Cl. ........................................ 514/18; 514/19;
530/331; 544/297; 544/322; 544/333; 546/293;
546/306; 546/332; 548/159; 548/188; 548/217;
548/228; 548/233; 548/237
[58] Field of Search .............. 514/18, 19; 530/331;
548/178, 180, 182, 184, 192, 194, 204, 217, 228,
233, 236, 159, 188, 237; 544/297, 322, 333;
546/299, 332, 306

[56] References Cited

U.S. PATENT DOCUMENTS

| | | | |
|---|---|---|---|
| 4,596,789 | 6/1986 | Dutta et al. | 514/19 |
| 4,643,991 | 2/1987 | Digenis et al. | 514/18 |
| 4,691,007 | 9/1987 | Dutta et al. | 514/19 |
| 4,880,780 | 11/1989 | Trainor et al. | 530/331 |
| 4,910,190 | 3/1990 | Bergeson et al. | 514/19 |

OTHER PUBLICATIONS

R. Graf, "Reactions with N-Carbonylsulfamoyl Chloride", *Angew. Chem. Internat. Edit.* (1968), 7, 172–182.
Chemical Abstracts, vol. 95, No. 25, 21st Dec. 1981, p. 223, abstract No. 216963a, Columbus, Ohio, U.S.; B. M. Ashe et al.: "Selective inhibition of human leukocyte elastase and bovine alpha-chymotrypsin by novel heterocycles", J. Biol. Chem. 1981, 256(22), 11603–6 *Abstract*.
Chemical Abstracts, vol. 97, No. 7, 16th Aug. 1982, p. 268, abstract No. 51652z, Columbus, Ohio, U.S.; T. Teshima et al.: "A new class of heterocyclic serine protease inhibitors. Inhibition of human leukocyte elastase, porcine pancreatic elastase, cathepsin G, and bovine chymotrypsin A, with substituted benzoxazinones, quinazolines, and anthranilates", J. Bio. Chem. 1982, 257(9), 5085–5091 *Abstract*.

*Primary Examiner*—Robert T. Bond
*Assistant Examiner*—Edward C. Ward
*Attorney, Agent, or Firm*—Rosemay M. Miano; Thomas E. Jackson

[57] ABSTRACT

The invention provides a series of novel heterocyclic ketones of formula I

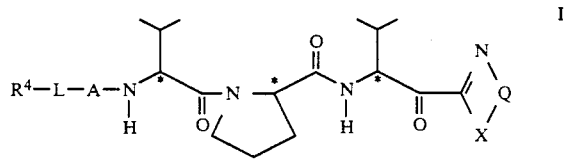

and pharmaceutically acceptable base-addition salts thereof, in which the values of R$^4$, L, A, X and Q have the meanings defined in the following specification. The compounds of formula I are inhibitors of human leukocytic elastase. The invention also provides pharmaceutical compositions containing a compound of formula I, or a pharmaceutically acceptable base-addition salt thereof, and processes and intermediates for the manufacture of compounds of formula I.

13 Claims, No Drawings

HETEROCYCLIC KETONES

BACKGROUND AND SUMMARY OF THE INVENTION

The activity of proteolytic enzymes of the elastase type has been implicated in several pathological conditions, for example in arthritis and in pulmonary emphysema. Pharmacological inhibition of an elastase enzyme would be expected to prevent or ameliorate an associated pathological condition. Trifluoromethyl ketone substituted peptide derivatives which are inhibitors of human leukocytic elastase are described in European Patent Application, Publication number 189305 A2.

The present invention relates to certain heterocyclic ketones which are human leukocyte elastase (HLE) inhibitors making them useful whenever such inhibition is desired, such as for research tools in pharmacological, diagnostic and related studies and in the treatment of tissue degenerative diseases such as, for example, pulmonary emphysema in mammals. The invention also includes intermediates useful in the synthesis of these heterocyclic ketones, processes for preparing them, pharmaceutical compositions containing such heterocyclic ketones and methods for their use.

DESCRIPTION OF THE INVENTION

According to the invention there are provided compounds of formula I (Formula set out on pages following Examples)     I wherein the group —Q— is selected from a group consisting of (i) ortho-phenylene, optionally bearing one or two substituents independently selected from a group consisting of halogeno, nitro, an amino group of formula —NR$^g$R$^h$, an acylamino group of formula —NHCOR$^m$, hydroxy, an acyloxy group of formula —OCOR$^n$, (1-4C)alkoxy (1-4C)alkyl, trifluoromethyl, carboxy, cyano, [(1-4C)alkoxy]carbonyl, an aminocarbonyl group of formula —CONR$^p$R$^q$ (including formula —CONR$^p_2$ when R$^p$=R$^q$), sulfo, sulfonamido of formula SO$_2$NR$^i$R$^j$ and (1-3C)hydroxyalkyl: and (ii) a cis-vinylene group of formula —C(R$^a$)=C(R$^b$)— wherein R$^a$ and R$^b$ are each independently selected from a group consisting of hydrogen, nitro, an amino group of formula —NR$^g$R$^h$, an acyloxy group of formula —O-COR$^n$, (1-4C)alkoxy, (1-6C)alkyl, trifluoromethyl, carboxy, cyano, [(1-4C)alkoxy]carbonyl, an aminocarbonyl group of formula —CONR$^p$R$^q$ (including formula —CONR$^p$ when R$^p$=R$^q$), a hydroxymethyl group, and phenyl optionally bearing one or two substituents chosen from a group consisting of halogeno, nitro, (1-4C)alkoxy, (1-4C)alkyl and trifluoromethyl:

R$^g$, R$^h$, R$^i$, R$^j$, R$^m$, R$^p$ and R$^q$ are each independently selected from a group consisting of hydrogen and (1-4C)alkyl:

R$^n$ is (1-4C)alkyl;

X is selected from a group consisting of oxygen and sulfur:

A is selected from a group consisting of —CO—, —NH.CO— and —O.CO—;

L is selected from a group consisting of phenylene, (1-6C)alkanediyl, (2-6C)alkenediyl and phenylene(1-3-C)alkyl, optionally containing one double bond in the alkyl portion, with the condition that a carbon included in a double bond of an alkenediyl or included in an optional double bond of a phenylenealkyl group is not directly bonded to an oxygen or nitrogen atom of group A; and R$^4$ is selected from a group consisting of acylsulfonamide of formula R$^5$.S(O$_2$).NH.CO—, acylsulfonamide of formula R$^5$.CO.NH.S(O$^2$)—, sulfonylurea of formula R$^5$.NH.CO.NH.S(O$_2$)—, sulfonylurea of formula R$^5$.S(O$_2$).NH.CO.NR$^6$—, and trifluoromethylsulfonamide of formula CF$_3$.S(O$_2$).NH— wherein R$^5$ is selected from a group consisting of (1-19C)alkyl; trifluoromethyl (3-10C)cycloalkyl; (6 or 10C)aryl optionally substituted by 1 to 3 members of a group consisting of halogeno, nitro, amino, dimethylamino, hydroxy, methyl, trifluoromethyl, carboxy, phenyl, and [(1-5C)alkylcarbonyl]amino; and an aromatic heterocyclic group defined as herein below in which up to 3 carbons of the aromatic system may bear a substituent group independently selected from a group consisting of halogeno and trifluoromethyl; and R$^6$ is hydrogen or methyl: and the pharmaceutically acceptable base-addition salts thereof.

In this specification, the following definitions are used, unless otherwise described:

Halogeno is fluoro, chloro, bromo or iodo.

Aromatic heterocyclic group means a group of from 1 to 15 carbons and from 1 to 4 heteroatoms each of which is independently selected from a group consisting of sulfur, nitrogen and oxygen, and which form 1 to 3 five- or six-membered rings, at least one of which is aromatic. More particularly, such an aromatic heterocyclic group is a monocyclic or fused bicyclic ring system of from 1 to 10 carbon atoms and from 1 to 4 heteroatoms.

Alkyl, alkanediyl, alkenediyl, etc. denote both straight and branched groups.

The radicals R$^4$, L and Q may contain chiral centers. The present invention includes compounds of formula I wherein chiral centers included in R$^4$, L and Q are of the R and/or S configurations. The radical L may contain a double bond: the present invention includes compounds of formula I wherein a double bond included in L is of the E and/or Z configuration.

The compounds of the invention of formula I can be viewed as tripeptidoyl heterocycles. In general, the preferred compounds of the present invention are of the naturally occurring L-amino acid configuration at the chiral centers identified by * in formula I. The methods of synthesis described below may provide a diastereomeric mixture as a result of the presence of products with both the R and the S configurations at the chiral center identified by # in formula I. While these diastereomers may be separated, it is not necessary to do so. The preferred compounds are those assigned the S configuration at the chiral center identified by #.

As will be appreciated by those skilled in the art, the activity of the individual isomers is not the same, and it is therefore preferred to utilize the more active isomer. The present invention includes both the diastereomeric mixture and the active S and R isomers.

A particular value for an optional substituent on Q when Q is o-phenylene, or for an optional substituent on R$^a$ or R$^b$ when R$^a$ or R$^b$ is phenyl, or for R$^g$, R$^h$, R$^i$, R$^j$, R$^m$, R$^n$, R$^p$ or R$^q$ when the substituent or group is (1-4-C)alkyl is, for example, methyl, ethyl, propyl, isopropyl, 2-methylpropyl or t-butyl. A particular value for an optional substituent on Q when Q is o-phenylene, or for $R^a$ or $R^b$, or for an optional substituent on $R^a$ or $R^b$ when $R^a$ or $R^b$ is phenyl when the substituent or group is (1-4C)alkoxy is, for example, methoxy, ethoxy, propoxy, isopropoxy, 2-methylpropoxy or t-butoxy. A particular value for an optional substituent on Q when Q is o-phenylene or for $R^a$ or $R^b$ when the substituent or group is [(1-4C)alkoxy]carbonyl is, for example, methoxycarbonyl, ethoxycarbonyl, isopropoxycarbonyl or t-butyoxycarbonyl. A particular value for $R^a$ or $R^b$, when it is (1-6C)alkyl is, for example, methyl, ethyl, propyl, isopropyl, butyl, 2-methylpropyl, t-butyl, pentyl, 3-methylbutyl or hexyl. A particular value for an optional substituent on Q when Q is o-phenylene or for an optional substituent on $R^a$ or $R^b$ when $R^a$ or $R^b$ is phenyl when the substituent is halogeno is, for example, fluoro, chloro or bromo.

A particular value for a (1-3C)hydroxyalkyl substituent on Q when Q is o-phenylene is, for example, hydroxymethyl, 2-hydroxyethyl or 1,1-dimethylhydroxymethyl.

A particular value of $R^5$ when $R^5$ is (1-10C)alkyl is, for example, methyl, ethyl, propyl, isopropyl, t-butyl or 4-methylpentyl. A particular value of $R^5$ when $R^5$ is (3-10C)cycloalkyl is, for example, cyclopropyl, cyclopentyl, cyclohexyl, norbornyl, or adamantyl. A particular value for $R^5$ when $R^5$ is (6 or 10C)aryl is, for example, phenyl or naphthyl; a particular value for an optional substituent on aryl when the substituent is halogeno is, for example, fluoro, chloro or bromo: and a particular value for an optional substituent on aryl when the substituent is [(1-5C)alkylcarbonyl]amino is, for example, formylamino, acetylamino, 2-methylpropanoylamino or 2,2-dimethylpropanoylamino. A particular value for $R^5$ when $R^5$ is an aromatic heterocyclic group is, for example, furyl, thienyl, pyridyl or pyrimidinyl: and a particular value for an optional substituent when the substituent is halogeno is, for example, fluoro, chloro or bromo.

A particular value for L when L is phenylene is, for example, p-phenylene or m-phenylene. A particular value for L when L is (1-6C)alkanediyl is, for example, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl or pentan-1,5-diyl. A particular value for L when L is (2-6C)alkenediyl is, for example, ethen-1,2-diyl, propen-1,2-diyl, propen-1,3-diyl, buten-1,4-diyl, but-2-en-1,4-diyl, penten-1,5-diyl or 3,3-dimethylpropen-1,3-diyl. A particular value for L when L is phenylene(1-3C)alkyl is, for example, p-phenylenemethyl, 2-(p-phenylene)ethyl or 2-(p-phenylene)-2-propyl: and when the phenylene-(1-3C)alkyl group contains an optional double bond, a particular value for L is, for example 2-(p-phenylene)ethenyl.

A more particular value for an optional substituent on Q when Q is o-phenylene is, for example, chloro, dimethylamino, acetylamino, hydroxy, acetoxy, methoxy, methyl, trifluoromethyl, carboxy, cyano, methoxycarbonyl, ethoxycarbonyl, aminocarbonyl, methylaminocarbonyl, dimethylaminocarbonyl, aminosulfonyl, dimethylaminosulfonyl or hydroxymethyl, including hydroxy, methoxy, carboxy, methoxycarbonyl, aminocarbonyl and hydroxymethyl.

A more particular value for $R^a$ or $R^b$ is, for example, hydrogen, dimethylamino, acetoxy, methoxy, methyl, trifluoromethyl, cyano, methoxycarbonyl, aminocarbonyl, methylaminocarbonyl, dimethylaminocarbonyl, hydroxymethyl, phenyl, chlorophenyl, methoxyphenyl, or trifluoromethylphenyl, including hydrogen.

A more particular value for $R^4$ is $R^5.S(O_2).NH.CO—$, $R^5.S(O_2).NH.CO.NR^6—$, or $CF_3SO_2NH—$.

A more particular value for $R^5$ is, for example, methyl, ethyl, isopropyl, cyclopropyl, cyclopentyl, phenyl, chlorophenyl, bromophenyl, trifluoromethylphenyl, 1-naphthyl, 2-thienyl, 2-pyridyl, or chloropyridyl, including methyl, isopropyl, phenyl and 4-chlorophenyl.

A more particular value for $R^6$ is hydrogen.

A more particular value for A is —CO—.

A more particular value for L is, for example, P-phenylene, ethane-1,2-diyl, ethen-1,2-diyl, p-phenylenemethyl or 2-(p-phenylene)ethenyl, including p-phenylene.

The particular values listed for radicals, substituents and ranges are for illustration only and do not exclude other defined values or other values within defined ranges for the radicals and substituents.

Within the scope of the invention are subgroups, including those in which the heterocyclic ring system containing N, Q and X is:

(a) a benzoxazole wherein X is oxygen and Q is o-phenylene as defined above under (i) in the definition of Q:

(b) an oxazole wherein X is oxygen and Q is cis-vinylene as defined above under (ii) in the definition of Q:

(c) a benzothiazole wherein X is sulfur and Q is o-phenylene as defined above under (i) in the definition of Q: and (d) a thiazole wherein X is sulfur and Q is cis-vinylene as defined above under (ii) in the definition of Q.

A value of X in formula I of particular interest is oxygen. Values for $R^4.L.A—$ in formula I of particular interest include for $R^4$: $R^5.S(O_2).—NH.CO—$ and $R^5.S(O_2).NH.CO.NR^6—$, especially $R^5.S(O_2).NH.CO—$; for L: p-phenylene: and for A: -CO-. A value of $R^5$ of particular interest is 4-chlorophenyl.

Specific compounds of formula I are described in the accompanying Examples. Compounds which are preferred include:

(i) [4-[(4-Chlorophenyl)sulfonylaminocarbonyl]benzoyl]-L-valyl-N-[1-(5-hydroxybenzoxazol-2-yl)carbonyl-2-methylpropyl]-L-prolinamide:

(ii) [4-[(4-Chlorophenyl)sulfonylaminocarbonyl]benzoyl]-L-valyl-N-[1-[5-(aminocarbonyl)benzoxazol-2-yl)carbonyl-2-methylpropyl]-L-prolinamide; and (iii) [4-[(4-Chlorophenyl)sulfonylaminocarbonyl]benzoyl]-L-valyl-N-[1-[5-(hydroxymethyl)benzoxazol-2-yl]carbonyl-2-methylpropyl]-L-prolinamide.

The salts of the compounds of formula I include pharmaceutically acceptable base-addition salts such as those derived from alkali metal hydroxides such as sodium hydroxide, alkali metal carbonates and bicarbonates, alkaline earth hydroxides and organic amines. Such salts may be prepared by dissolving the heterocyclic ketone in a mixture of water and a water-miscible organic solvent, adding an aqueous solution of the base and recovering the salt from the aqueous solution.

The compounds of formula I may be made by processes which include processes known in the chemical art for the production of structurally analogous heterocyclic and peptidic compounds. Such processes for the manufacture of a compound of formula I as defined above are provided as further features of the invention and are illustrated by the following procedures in which the meanings of generic radicals are as defined above (and a radical of formula Q may include a protecting group):

(A) For a compound of formula I, oxidizing a corresponding alcohol of formula III:

(Formula set out on pages following Examples)   III

Methods which are useful include the use of oxalylchloride, dimethyl sulfoxide, and a tertiary amine (see Marx, M. et al., *J. Org. Chem.*, 49, 788–793 (1984)): the use of acetic anhydride and dimethyl sulfoxide: the use of dimethyl sulfoxide, 1-(3-dimethylaminopropyl)-3-ethylcarbodiimide hydrochloride and dichloroacetic acid in, for example, toluene (see, e.g. Example 19); the use of chromium trioxide pyridine complex in methylene chloride; and the use of Dess-Martin periodinane [1,1,1-triacetoxy-2,1-benzoxiodol-3(3H)-one](method of Dess, D. B. et al, *J. Org. Chem.*, 48, 4155–56 (1983)). When Q has the value (i) ortho-phenylene and X is oxygen, generally a preferred oxidant is Dess-Martin periodinane; however, when Q bears an aminocarbonyl group, the use of chromium trioxide pyridine complex or of dimethyl sulfoxide, 1-(3-dimethylaminopropyl)-3-ethylcarbodiimide hydrochloride and dichloroacetic acid is preferred. When an alcohol of formula III contains a basic nitrogen, it is generally preferable to use an alternative method or to protect the basic nitrogen before oxidation and deprotect it after oxidation to provide the corresponding compound of formula I.

(B) For a compound of formula I wherein $R^4$ has the value $R^5.S(O_2).NH.CO-$, reacting a corresponding compound of formula IV (Formula set out in pages following Examples)   IV wherein $R^7$ is carboxy (which compound is hereinafter referred to as "acid of formula IV") with a sulfonamide derivative of formula $R^5.SO_2.NH_2$ in the presence of a dehydrating agent or reacting a reactive derivative of an acid of formula IV with a sulfonamide, or a salt thereof, of formula $R^5.SO_2.NH_2$. Thus, for example, a free acid of formula IV may be reacted with a suitable dehydrating agent, for example, with dicyclohexylcarbodiimide or 1-(3-dimethylaminopropyl)3-ethylcarbodiimide, or with a hydrochloride or hydrobromide salt thereof, optionally together with an organic base, for example, 4-dimethylaminopyridine, and with a sulfonamide of formula $R^5.SO_2.NH_2$ in the presence of a suitable solvent or diluent, for example, dichloromethane, at a temperature in the range of, for example, 0° to 50° C., but preferably at or near ambient temperature.

Alternatively, a reactive derivative of an acid of formula IV, for example, an acid halide (such as the acid chloride), acid anhydride or a mixed acid anhydride (such as that formed from N,N-diphenylcarbamic acid and the acid of formula IV by reaction of the sodium salt of the latter acid with N,N-diphenylcarbamoylpyridinium chloride), may be reacted with an alkali metal salt (such as the lithium, sodium or potassium salt) of the appropriate sulfonamide of formula $R^5.SO_2.NH_2$, conveniently at or near ambient temperature and in a suitable solvent or diluent, for example, tetrahydrofuran, N,N-dimethylformamide or dichloromethane.

(C) For a compound of formula I wherein $R^4$ has the value $R^5.CO.NH.S(O_2)-$, reacting a corresponding compound of formula IV in which $R^7$ has the value $H_2N.S(O_2)-$ with an acid of formula $R^5.COOH$ using a similar method to one of those described above in part (B).

(D) For a compound of formula I wherein $R^4$ has the value $R^5.NH.CO.NH.S(O_2)-$, reacting a corresponding compound of formula IV in which $R^7$ has the value $H_2N.S(_2)-$ with an isocyanate of formula $R^5.NCO$. For example, an intermediate of formula IV in which $R^7$ is $H_2N.S(O_2)-$ may be treated with phenylisocyanate to provide a corresponding product of formula I in which $R^5$ is phenyl.

(E) For a compound of formula I wherein $R^4$ has the value $R^5.S(O_2).NH.CO.NR^6-$, reacting a corresponding compound of formula IV in which $R^7$ has the value $HNR^6-$ with a sulfonylisocyanate of formula $R^5.S(O_2).NCO$; or alternatively, for a compound in which $R^6$ has the value H, reacting a corresponding compound of formula IV in which $R^7$ has the value $-NCO$ with a sulfonamide of formula $R^5.S(O_2).NH_2$. The reaction may be carried out, for example, at room temperature in a suitable inert organic solvent such as tetrahydrofuran or dichloromethane.

(F) For a compound of formula I wherein $R^4$ has the value $CF_3.S(O_2).NH-$, reacting a corresponding amine of formula IV in which $R^7$ has the value $H_2N-$ with trifluoromethanesulfonic anhydride, for example, at 0° in an inert solvent such as dichloromethane.

(G) For a compound of formula I wherein A has the value $-CO-$, coupling an acid of formula $R^4-L-COOH$ (or a reactive derivative thereof) with an amino ketone of formula V:

(Formula set out on pages following Examples)   V

For example, the coupling may be carried out using 1-(3-dimethylaminopropyl)-3-ethylcarbodiimide hydrochloride and 4-dimethylaminopyridine or 1-hydroxybenzotriazole in an inert solvent such as tetrahydrofuran. Similarly, a compound of formula I wherein A has the value $-NH.CO-$ or $-O.CO-$ may be prepared from a corresponding amino ketone of formula V using a similar method to one described below for the preparation of a starting material alcohol of formula III from an amino alcohol of formula XV.

It may be desired to optionally use a protecting group during all or portions of the above described processes; the protecting group then may be removed when the final compound or a required starting material is to be formed, for example, as described in Examples 5 and 7.

Whereafter, modifying a functional group of a compound of formula I by a conventional method to afford a different compound of formula I, such as, for example, converting an optional carboxy or alkoxycarbonyl substituent on Q to an aminoacyl substituent, may be carried out.

Whereafter, for any of the above procedures, when a pharmaceutically acceptable salt is required, it may be obtained by reaction of the acidic form of a compound of formula I with a base comprised of a physiologically acceptable cation and a physiologically acceptable anion and affording a physiologically acceptable cation or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples.

As will be clear to one skilled in the art, a variety of sequences is available for preparation of the starting materials. According to one of the available routes, a key intermediate of formula XI may be prepared as shown in Scheme I (set out on pages following Examples) beginning with valinol (formula VII) and utilizing the intermediates of formulae VIII, IX and X as described in Example 1. Alternatively, valinol (formula VII) may be coupled with an acid of formula IX to afford an alcohol of formula XII; and an alcohol of formula XII may be oxidized to provide an aldehyde of formula XI as a key intermediate.

As shown in Scheme II (set out on pages following Examples) an intermediate aldehyde of formula XI may be converted into a starting material alcohol of formula III, a starting material ketone of formula IV or a starting material amino ketone of formula V.

An aldehyde of formula XI may be reacted with, for example, an alkalai metal cyanide, such as, for example, sodium cyanide or potassium cyanide, to form a cyanohydrin of formula XIII wherein W is CN. More preferably, an aldehyde of formula XI may be converted into a cyanohydrin formula XIII wherein W is CN by treatment with acetone cyanohydrin, for example as described in Example 4a. In addition, trimethylsilylcyanide may be used for the transformation, the trimethylsilyl group being removed upon acidic workup. The hydroxy group of such a cyanohydrin may optionally be protected by, for example, an acetyl group or a trimethylsilyl or t-butyldimethylsilyl group.

A cyanohydrin of formula XIII wherein W is CN may be converted into a corresponding heterocyclic alcohol of formula XIV, either directly or via an isolated intermediate using a conventional method. For example, conversion of a compound of formula XIII wherein W is CN into a corresponding compound of formula XIV wherein Q has the value o-phenylene as defined above may be carried out using a similar procedure to one described in Hölljes, E. L. and Wagner, E. C., $J.$ $Org.$ $Chem.,$ (1944), 9, 31. Conversion of a compound of formula XIII wherein W is CN into a corresponding compound of formula XIV wherein Q has the value cis-vinylene as defined above may be carried out using a similar procedure to one described in Lora-Tamato, M. et al, $Chem.$ $Ber.,$ (1964), 97, 2230, 2234 or in Kitatani, K. et al, Tet. Lett., (1974), 1531.

Alternatively, a cyanohydrin of formula XIII wherein W is CN may be transformed into an imidate of formula XIII where W is —C(NH)OR and R is, for example, methyl or ethyl, preferably as its, for example, hydrochloride salt. An imidate of formula XIII wherein W is -C(NH)OR may be transformed into a corresponding heterocyclic alcohol of formula XIV; the intermediate imidate may be optionally isolated. The chemistry of imidates has been reviewed in "The Chemistry of Amidines and Imidates," Saul Patai, Ed., John Wiley and Sons, N.Y., 1975, p. 385 and in Roger, R. and Nielson, D. G., $Chem.$ $Rev.,$ (1961), 61, 1979. Conversion of an imidate of formula XIII wherein W is -C(NH)OR into a corresponding compound of formula XIV wherein Q has the value o-phenylene as defined above under (i) in the definition of Q may be carried out using a similar procedure to one described in King, F. E. and Acheson, R. M., $J.$ $Chem.$ $Soc.,$ (1949), 1396: or in Reid, W. et al, $Liebigs$ $Ann.$ $Chem.,$ (1964), 676, 114. Conversion of a compound of formula XIII wherein W is —C(NH)OR into a corresponding compound of formula XIV wherein Q has the value cis-vinylene as defined above under (ii) in the definition of Q and X is oxygen may be carried out using a similar procedure to one described in Wiley, R. H., $Chem.$ $Rev.,$ (1945), 37, 401; or in Cornforth, J. W., and Cornforth, R. H., $J.$ $Chem.$ $Soc.,$ (1947), 96: (1953), 93.

As a further alternative, an imidate of formula XIII wherein W is —C(NH)OR may be hydrolyzed to the corresponding ester of formula XIII wherein W is —COOR. By using an ester of formula XIII wherein W is —COOR, a corresponding acid of formula XIII wherein W is —COOH (available by hydrolysis of the ester in a conventional manner), or a different activated derivative of an acid of formula XIII wherein W is COOH, and a conventional method, a corresponding compound of formula XIV may be prepared. For example, for a compound of formula XIV wherein Q is o-phenylene as defined above under (i) in the definition of Q, a similar method to one described in Landenberg, A., $Chem.$ $Ber.,$ (1876), 9, 1524: in Galatis, L. C., $J.$ $Amer.$ $Chem.$ $Soc.,$ (1948), 70, 1967; in "Heterocyclic Compounds", Vol. 5, R. C. Elderfield, Ed., J. Wiley & Sons, N.Y., 1957, p. 421 in Lankezma, H. P. and Knauf, A. E., $J.$ $Amer.$ $Chem.$ $Soc.,$ (1931), 53, 309 and 2654: in Lankezma, H. P. and Vopicka E., ibid., (1936), 58, 609: or in "The Chemistry of Heterocyclic Compounds," P. N. Preston, Ed., (1981), 40, 6–12 may be used. For example, for a compound of formula XIV wherein Q is cis-vinylene as defined above under (ii) in the definition of Q and X is oxygen, a similar method to one described in Wasserman, H. H. and Lu, T.-J., Tet. Lett., (1982), 3831; in Davidson, D. et al, $J.$ $Org.$ $Chem.,$ (1937), 2, 328; or in Weigand, E. E. and Rathburn, D. W., $Synthesis,$ (1970) 648 and $J.$ $Chem.$ $Eng.$ $Data,$ (1973), 18, 237 may be used. For example, for a compound of formula XIV wherein Q is cis-vinylene as defined above under (ii) in the definition of Q and X is sulfur, a similar method to one described in Gabriel, S., $Chem.$ $Ber.,$ (1910), 43, 134 and 1283: in Bachstez, M., ibid. (1947), 47 3163; or in Wiley, R. H. et al, $Org.$ $Reactions,$ (1951), 6, 367 may be used.

Another alternative for the preparation of certain compounds of formula XIV wherein X is sulfur is the use of a thioamide of formula XIII wherein W is —CSNH$_2$. A thioamide of formula XIII wherein W is —CSNH$_2$ may be obtained, for example, from a corresponding nitrile in a conventional manner, such as, for example, treatment with hydrogen sulfide, optionally employing a basic catalyst, such as, for example, triethylamine. Thus, for example, a thioamide of formula XIII wherein W is —CSNH$_2$ may be converted into a corresponding compound of formula XIV wherein Q is cis-vinylene as defined above under (ii) in the definition of Q and X is sulfur by using a similar method to one described in Schmidt, V. et al, $Synthesis,$ (1986), 992 or in Wiley, R. H. et al, $Org.$ $Reactions,$ (1957), 6, 367 and 378.

A different route from an aldehyde of formula XI to a heterocyclic alcohol of formula XIV involves the use of a preformed heterocyclic reagent. For example, an organolithium reagent of formula XVI wherein Y is lithium may be reacted directly with an aldehyde of formula XI to provide a corresponding alcohol of formula XIV. When X is oxygen, it may be preferred or necessary to use a different method. Reagents of formula XVI wherein Y is lithium may be prepared and used as described, for example, in Wasserman, H. H. et al, Tet. Lett., (1981), 22, 1737; in Schroeder, R. et al, $Liebigs$ $Ann.$ $Chem.,$ (1975), 533; in Beraud, J. and Metzger, J., $Bull.$ $Soc.$ $Chem.$ $France,$ (1962), 2072; in Shirlet, D. A. and Alley, P. W., $J.$ $Amer.$ $Chem.$ $Soc.,$ (1957), 79, 4922: in Ogura, H. and Takahashi, H., $J.$ $Org.$

*Chem.*, (1974), 39, 1374: in Justin, P. and Hoffmann, H. J., *Chem. Ber.*, (1973), 106, 594: and in Justi, P. and Sakriss, W., ibid., (1973), 106, 2815.

Alternatively, for example, a Z-trimethylsilyl heterocyclic reagent of formula XVI wherein Y is trimethylsilyl may be condensed with an aldehyde of formula XI to provide an intermediate o-trimethylsilyl derivative of a corresponding alcohol of formula XIV. The alcohol of formula XIV may then be obtained by removal of the trimethylsilyl group using a conventional procedure. Reagents of formula XVI wherein Y is trimethylsilyl may be prepared and used in a manner similar to those described, for example, for 4-methyl-2-trimethylsilyloxazole, 2-trimethylsilylbenzothiazole and 2-trimethylsilylthiazole in A. Dondoni, et al, *Tet. Lett.*, (1985), 26, 5477: in A. Dondoni et al, *J. Chem. Soc., Chem. Commun.*, (1984), 258: and in A. Medici et al, *Tet. Lett.*, (1983), 24, 2901.

By using a procedure similar to one described in Levin, J. I. and Weinreb, S. M., *J. Org. Chem.*, (1984), 49, 4325, an oxazole of formula XIV wherein X is oxygen and Q is cis-vinylene as defined above under (ii) in the definition of Q may be prepared from a corresponding oxazoline (4,5-dihydrooxazole). The oxazoline may be prepared, for example, in a conventional manner from a corresponding intermediate of formula XIII wherein W is CN, —C(NH)OR, —COOR, or —COOH, or by reaction of an appropriate organometallic reagent with a corresponding compound of formula XI. (Thiazolines may similarly be prepared and dehydrogenated to afford thiazoles of formula XIV wherein X is sulfur and Q is cis-vinylene as defined under (ii) in the definition of Q.)

An alcohol of formula XIV may be converted into a corresponding amino alcohol of formula XV by removal of the CBZ-group using a conventional method, such as, for example, hydrogenolysis over a palladium on carbon catalyst at about 3 bars pressure and ambient temperature in an appropriate solvent such as, for example, ethanol.

An amino alcohol of formula XV may be converted into a starting material of formula III by reacting the amino alcohol of formula XV with an appropriate acylating agent. For example, when A is —CO—, appropriate acylating agents are activated derivatives of acids of formula $R^4$.L.COOH, for example, activated derivatives thereof generated in situ when using conventional coupling reagents, such as, for example, 1-(3-dimethylaminopropyl)-3-ethylcarbodiimide hydrochloride and 1-hydroxybenzotriazole or 4-dimethylaminopyridine, as well as, for example, acid chlorides of formula $R^4$.L.COCl. When A is —NH.CO—, appropriate acylating agents include isocyantes of formula $R^4$.L.NCO. When A is —O—CO—, appropriate acylating agents include chloroformates of formula $R^4$.O.CO.Cl. In general, the acylation is performed in an inert diluent or solvent, such as dichloromethane, tetrahydrofuran or dioxane, and at a temperature in the range of, for example, 0°–60°. An organic or inorganic base such as triethylamine, 4-methylmorpholine, 4-dimethylaminopyridine, potassium carbonate or sodium hydroxide may also conveniently be used as an acid acceptor when appropriate.

Starting material ketones of formula IV may also be obtained from an intermediate alcohol of formula XV as shown in Scheme II. Thus, for example, for a starting material of formula IV wherein $R^7$ has a value of $R^zO_2C$—, $H_2N.SO_2$—, or $R^6NH$— and $R^z$ has a value defined below, an amino alcohol of formula XV may be converted into a corresponding alcohol of formula XVII by using a method analogous to one described above for preparation of a compound of formula III and an analogous reagent, such as, for example $R^7$.L.COOH, $R^7$.L.COCl, $R^7$.L.NCO or $R^7$.L.O.COCl. Then, by using a similar oxidation process to one described in process (A), an alcohol of formula XVII may be oxidized to provide a starting material ketone of formula IV. A starting material ketone of formula IV wherein $R^7$ has a value of —NCO may be prepared from a corresponding ketone of formula IV wherein $R^7$ is carboxy by use of a modified Curtius reaction using, for example, diphenylphosphorylazide and triethylamine in benzene or toluene at 80° (See T. Shioiri, K. Ninomiya and S. Yamada, *J. Amer. Chem. Soc.*, (1972), 94, 6203). A starting material of formula IV wherein $R^7$ has the value carboxy may be prepared by decomposing a suitable, corresponding ester of formula IV wherein $R^7$ has the value $R^zO_2C$— in which $R^z$ is a conveniently removed acid protecting group, for example, phenyl, benzyl, or (1–6C)alkyl optionally bearing an acetoxy, (1–4C)alkoxy or (1–4C)alkylthio substituent.

A particular value for $R^z$ is, for example, methyl, ethyl, propyl, t-butyl, acetoxymethyl, methoxymethyl, 2-methoxyethyl, methylthiomethyl, phenyl, or benzyl.

It will be appreciated that the decomposition of an ester of formula IV wherein $R^7$ is $R^zO_2C$— can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Alternatively, in certain circumstances, for example, when $R^z$ is t-butyl, it may be preferred to carry out the decomposition using acid catalysis, for example, by treating an ester of formula IV with, for example, trifluoroacetic acid at a temperature of, for example, 0°–40° C., in a suitable solvent or diluent such as dichloromethane. In addition, when $R^z$ is t-butyl, the decomposition may be performed, for example, by using trimethylsilyl triflate and then water, in a conventional manner. Still further, in certain circumstances, for example, when $R^z$ is benzyl, it may be possible to carry out the decomposition by reductive means, for example, by the use of hydrogen at a pressure of about three bars in the presence of a suitable catalyst, such as palladium or platinum, conveniently on charcoal as a support.

Starting material amino ketones of formula V may be obtained from corresponding alcohols of formula XIV via the corresponding ketones of formula VI. Thus, by using an oxidation procedure similar to one described above in method (A), an alcohol of formula XIV may be oxidized to a corresponding ketone of formula VI, for example, as described in Example 7d and Example 8b. Removal of the N-protecting group from a ketone of formula VI will then provide a corresponding starting material amino ketone of formula V. The protecting group conveniently may be removed using, for example, trifluoromethanesulfonic acid in dichloromethane at room temperature. It is convenient to isolate an amino ketone of formula V so prepared as its crude trifluoromethanesulfonic acid salt and use it directly for the preparation of a corresponding product of formula I, for example, as described in Example 7f. If an amino ketone of formula V is isolated in the form of its free base, for example as described in Example 8c, it is preferable to use the material at once because of the limited stability of the free base.

Starting material ketones of formula IV may also be prepared from corresponding amino ketones of formula V using analogous methods to those described above for the preparation of alcohols of formula XVII from corresponding alcohols of formula XV.

An alternative, analogous approach to the starting materials of formulae III, IV and V is outlined in Scheme III (set out on pages following Examples). A protected valinal, for example CBZ-valinal, may be converted into a corresponding protected heterocyclic alcohol of formula XIVa by using a method analogous to one described above for the conversion of a protected aldehyde of formula XI into a protected heterocyclic alcohol of formula XIV. The conversion may be carried out stepwise through analogous intermediates of formula XIIIa or directly by using a heterocyclic reagent of formula XVI. An alcohol of formula XIVa may be deprotected to provide an amino alcohol of formula XVa. By coupling with an acid of formula IX, an amino alcohol of formula XVa may be converted into an alcohol of formula XIV to be used as described in Scheme II. Alternatively, an amine of formula XVa may be coupled with an acid of formula IXa (prepared by using standard methods or methods analogous to those described above) to provide a starting material of formula III, for example, as described in Example 19. In addition, an amine of formula XVa may be coupled with an acid of formula IXb (prepared by using standard methods or methods analogous to those described above) to provide a compound of formula XVII, which may be converted into a starting material of formula IV.

A further approach to starting materials of formulae IV and V, as well as to compounds of formula I, also involves the use of organometallic reagents of formula XVI wherein Y is lithium, especially when X is sulfur, as illustrated in Scheme IV and Example 13 and Example 14. Thus, for example, a suitably aminoprotected, N,N-disubstituted valinamide, such as benzyloxycarbonyl protected, N-methoxy-N-methylvalinamide of formula XX, may be treated with a lithiated heterocycle, such as 2-lithiothiazole or 2-lithiobenzothiazole, to afford a corresponding ketone of formula XXI. Removal of the amino-protecting group from a compound of formula XXI by a conventional method affords a corresponding aminoketone of formula XXII. By coupling an acid of formula IX with an amine of formula XXII, a corresponding ketone of formula VI may be obtained. As described above, a ketone of formula VI may be converted into a starting material of formula V, which starting material of formula V may be further converted into a starting material of formula IV. By coupling an acid of formula IXa with an amine of formula XXII, a corresponding product of formula I may be obtained. Similarly, by coupling an acid of formula IXb with an amine of formula XII a corresponding starting material of formula IV may be obtained directly. Also, by use of analogous methodology to that described for the conversion of an amide of formula XX into an amino ketone of formula XXII, other intermediate compounds, such as those of formula XXIII, formula V and formula IV wherein $R^7$ is $HNR^6$—, may be obtained.

As will be clear to one skilled in the art, the order of steps in the sequences leading to the starting materials and products of the invention may be altered if appropriate considerations relative to coupling methods, racemization, deprotection methods, etc. are followed.

Inhibition Measurements

The potency of compounds of the invention to act as elastase inhibitors is initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinylalanyl-alanyl-prolyl-valine-p-nitroanilide as described by Nakajima, K. et al. in *J. Biol. Chem.*, 245, 4027–4032 (1979) and by Teshima, T. et al. in *J. Biol. Chem.*, 257, No. 9, 5085–5091 (1982). The HLE enzyme used in these studies may be obtained from Elastin Products of St. Louis, Miss. or can be purified according to Viscarello, B. R. et al. in *Preparative Biochemistry*, Vol. 13, pages 57–67, (1983) as also described in European Patent Application, Publication number 189305 A2. From the thus purified HLE, a standard rate of production of p-nitroaniline was measured at 25° C. spectrophotometrically in the visible spectrum at 410 nanometers with automatic data acquisition from a a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

In general, the heterocyclic ketones of the present invention are not "slow-binding" inhibitors of HLE: however, if the heterocyclic ketones are found to be "slow-binding" inhibitors of HLE, special methods of analysis to accurately determine $K_i$ values for their inhibition of HLE are carried out. (See Williams, J. W. and Morrison, J. F., *Meth. Enz.* 63, 437 (1979) for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO are added to a 3 milliliter cuvette. The cuvette is stoppered, inverted several times to mix its contents and maintained at (25° C) in the spectrophotometer. After a period of five minutes to allow the reaction solution to come to thermal equilibrium, 10 microliters of stock enzyme solution are added to the cuvette to initiate the reaction. Duplicate or triplicate runs are done at zero inhibitor concentration and at least three non-zero inhibitor concentrations. $K_i$ values are calculated according to methods outlined in the above reference by Williams and Morrison. The $K_i$ values for selected compounds are less than $10^{-7}M$. For example, the $K_i$ value for the compound of Example 1 is $3.3 \times 10^{-10}M$.

Animal Models

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing 400 μg of human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavagable cells relative to HLE alone.

Compounds of the present invention which were tested exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavagable cells and wet lung weights relative to the administration of HLE alone obtained in the Animal Model test. In general, no overt signs of acute toxicity were noticed for compounds of the present invention tested in the Animal Model.

The compounds of the present invention may be administered to a warm-blooded animal in need thereof for treatment of a tissue degenerative disease, particularly a human, in particular for the treatment of emphysema. The preferred mode of administration may be via a powdered or liquid aerosol. In a powdered aerosol, compounds of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a compound of the invention with the remainder of the 20 mg capsule being a pharmaceutically acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the conditions being treated, the weight of the patient and the particular size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy," Lea and Febiger, Philadelphia (1976).

Alternatively, the mode of administration may be oral or parenteral, including subcutaneous deposit by means of an osmotic pump. The compounds of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 ml intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

The invention will now be illustrated by the following non-limiting examples in which, unless stated otherwise:

(i) temperatures are given in degrees Celsius (C); operations were carried out at room or ambient temperature, that is, at a temperature in the range of 18°–25°;

(ii) evaporation of solvent was carried out using a rotary evaporator under reduced pressure (600–4000 pascals; 4.5–30 mm Hg) with a bath temperature of up to 60°;

(iii) flash chromatography was carried out on Merck Kieselgel (Art 9385) [obtained from E. Merck, Darmstadt, W. Germany]; if "acidic silica gel" is indicated, material custom prepared by J. T. Baker Chemical Co., Phillipsburg, NJ, USA, and having a pH of about 6 when slurried in water was used: thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only:

(v) melting points are uncorrected and (d) indicates decomposition: the melting points given are those obtained for the materials prepared as described; polymorphism may result in isolation of materials with different melting points in some preparations:

(vi) all final products were essentially pure by TLC and had satisfactory nuclear magnetic resonance (NMR) spectra and microanalytical data;

(vii) yields are given for illustration only and are not necessarily those which may be obtained by diligent process development: preparations were repeated if more material was required;

(viii) when given, NMR data is in the form of delta values for major diagnostic protons, given in parts per million (ppm) relative to tetramethylsilane (TMS) as an internal standard, determined at 80 MHz or 250 MHz using $CDCl_3$, DMSO-$d_6$ or $CD_3OD$ as solvent; conventional abbreviations for signal shape are used, for example: s, singlet: d, doublet; m, multiplet; br, broad: etc.: in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: min (minutes), hr (hours), v (volume), w (weight); mp (melting point), l [liter(s)], ml (milliliters), g [gram(s)], mg [milligram(s)]:

(xi) solvent ratios are given in volume: volume (v/v) terms: ratios of solids are given in weight:weight (w/w) terms;

(xii) mass spectra (MS) were run with an electron energy of 70 electron volts in the chemical ionizaton mode using a direct exposure probe; when given, only peaks ten percent of the base peak and larger are reported; and (xiii) when high pressure liquid chromatography (HPLC) data is reported, $t_R$ (retention time) is given in min, FR (flow rate) is given in ml/min, Col A is a 'Zorbax' (a trademark) ODS analytical column (4.6 mm ×25 cm) and Col B is a 'Phenomenex' (a trademark) 'Zorbax' C-8 analytical column (4.6 mm×35 cm). NOMENCLATURE: For uniformity and clarity, "amino acid sequence" type names are used whenever possible. In general, a stereochemical identification of a chiral center as (S) indicates that the product is estimated to contain at least 95% of the (S)-isomer at the center indicated: the absence of an identification of stereochemistry at a chiral center indicates a mixture of isomers which is not necessarily 1:1 at the center indicated.

EXAMPLE 1

(S)-[4-[(4-Chlorophenyl)sulfonylaminocarbonyl]benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, $R^4=R^5.S(O_2).NH.CO-$, $R^5=4-ClC_6H_4$).

a. N-Benzyloxycarbonyl-L-valinol

Benzyl chloroformate (91.0 g, 95% purity) was added dropwise over a period of 1 hr to a precooled (0°) solution of L-valinol (50.0 g) and triethylamine (60.0 g) in chloroform (1500 ml). The reaction mixture was stirred for 1 hr at 0° and then allowed to warm to room temperature over 2 hr. After the reaction mixture was evaporated, ethyl acetate (1500 ml) was added to the residue: and the organic solution was washed with 1N NaOH and brine, dried (MgSO4), and evaporated. The resulting residue purified by flash chromatography, using a stepwise gradient of ether:hexane (1:5) followed by ether, to give the product (91.4 g) as a white waxy solid; TLC, $R_f=0.23$, hexane:ether (50:50).

b. N-Benzyloxycarbonyl-L-valinal

A solution of dimethylsulfoxide (107.2 g) in methylene chloride (150 ml) was added dropwise over 0.5 hr to a precooled (−60°), stirred solution of oxalyl chloride (87.1 g) in methylene chloride (800 ml) under a nitrogen atmosphere. The temperature of the mixture rose to −45°. The reaction mixture was then warmed to −30°. A solution of the product of Example 1a (81.5 g) in methylene chloride (300 ml) was added dropwise over 45 min at −30°. The reaction mixture was stirred for 50 min at −25°, cooled to −40° and a solution of diisopropylethylamine (177.4 g) in methylene chloride (250 ml) was added dropwise over 45 min at −40°. The reaction mixture was stirred for 1 hr as it warmed to room temperature. The reaction mixture was diluted with methylene chloride (1500 ml), and the organic phase was washed with 1N HCl and evaporated to give the product (98 g) as a green oil which was used immediately without further purification; TLC, $R_f=0.48$, hexane:ether (50:50).

c. N-Benzyloxycarbonyl-L-valinal diethylacetal

Triethyl orthoformate (508 g), absolute ethanol (800 ml) and p-toluenesulfonic acid monohydrate (5.0 g) were added to a portion of the product of Example 1b (81 g). The mixture was stirred for 10 min at room temperature and then evaporated. The resulting residue was dissolved in ether, washed with saturated aqueous NaHCO3, dried (Na2SO4), and evaporated to give a crude product which was purified by flash chromatography using a stepwise gradient of hexane through mixtures of methylene chloride:hexane to ethyl acetate:methylene chloride (30:70) to give the product (84.7%) as a pale yellow oil; TLC, $R_f=0.21$, methylene chloride:petroleum ether (50:50).

d. L-Valinal diethylacetal (Formula VIII)

A mixture of the product prepared using the method of Example 1c (147.8 g) and 10% palladium on carbon (10 g) in ethyl acetate (1500 ml) was stirred under H2 (1 bar) until 2500 ml of H2 were consumed. Twice during this time the reaction was interrupted and 10% palladium on carbon (10 g) was added. The reaction mixture was then filtered through a pad of diatomaceous earth. 10% Palladium on carbon (10 g) was added and the reaction mixture was again stirred under H2 until 10.92 liters of H2 were consumed. The reaction mixture was filtered through diatomaceous earth and the filtrate was concentrated under vacuum to give the product (78.8 g) as a pale yellow oil; $a_D{}^{25}=+7.8$.

e. Benzyloxycarbonyl-L-valyl-L-proline methyl ester

To a cooled (0-5°) solution of N-benzyloxycarbonyl-L-valine (450.0 g) in dry N,N-dimethylformamide (3.0 liter) was added 1-hydroxybenzotriazole hydrate (483.3 g): and the reaction mixture was stirred for 20 min, followed by the addition of a slurry of L-proline methyl ester hydrochloride (296.4 g) and triethylamine (186.6 g) in N,N-dimethylformamide (1.5 liter). After the resulting mixture was cooled to 0°, 1-(3-dimethylaminopropyl)-3-ethylcarbodiimide hydrochloride (377.6 g, 1.97 mol) in N,N-dimethylformamide (500 ml) was added. The reaction mixture was stirred at 0°-5° for 3 hr and then allowed to warm gradually to room temperature. Stirring was continued for 65 hr, and the mixture was filtered and evaporated. The residue was partitioned between ether and 1N HCl, and the precipitate which formed was removed by filtration. The ethereal layer was then separated: washed with water, saturated aqueous NaHCO3 and brine; dried (MgSO4); and evaporated. The crude ester was purified by flash chromatography using a gradient elution of methylene chloride, then methanol:methylene chloride (1:99), (2.5:79.5), and, finally, (5:95). The impure material from the first column was rechromatographed using a gradient elution of methylene chloride:hexanes (1:3), methylene chloride, and, finally, methanol:methylene chloride (2:98). The combined chromatographies afforded the ester (596.9 g, 92%) as a colorless oil; TLC, $R_f=0.45$-0.60, methanol:methylene chloride (5:95); MS, m/e=363(M+1, base), 319, 255, 130, 91.

Analysis for $C_{19}H_{26}N_2O_5 \cdot 0.25$ H2O: Calculated: C, 62.19: H, 7.28: N, 7.68. Found: C, 62.19; H, 7.12; N, 7.51.

f. Benzyloxycarbonyl-L-valyl-L-proline (Formula IX).

To a solution of the product of Example 1e (595.0 g) in methanol (4.8 liter) was added 1N NaOH (1.80 liter), and the solution was stirred for 18 hr. The methanol was evaporated, and the aqueous layer was acidified (pH 2) with 1N HCl and extracted with methylene chloride. The organic extracts were washed with brine, dried ($Na_2SO_4$) and evaporated to afford the acid (520.2 g, 90%) as an analytically pure, white solid: MS, m/e=349(M+1, base), 305, 241, 206, 116, 91.

Analysis for $C_{18}H_{24}N_2O_{0.3}$ $H_2O$: Calculated: C, 61.11: H, 7.01: N, 7.92. Found: C, 61.12: H, 6.86: N, 7.68.

g.
(S)-Benzyloxycarbonyl-L-valyl-N-[1-(diethoxymethyl)-2-methylpropyl]-L-prolinamide (Formula X)

Isobutyl chloroformate (57.8 g) was added in one portion to a solution of the product of Example 1f (154.3 g) and 4-methylmorpholine (42.8 g) in dry tetrahydrofuran(280 ml) at −20°. After stirring for 10 min, the mixture was cooled to −40° and aminoacetal prepared as described in Example 1, parts a–d (74.2 g) in tetrahydrofuran(700 ml) was added. The mixture was allowed to warm to room temperature and stir for 16 hr before it was filtered and evaporated. The residue was dissolved in ethyl acetate; washed with 1N HCl, saturated aqueous $NaHCO_3$ and brine: dried ($Na_2SO_4$): and evaporated. The crude product was purified by flash chromatography eluting with a gradient of methylene chloride, then ethyl acetate: methylene chloride (4:96), (8:92), (25:75), (50:50), and, finally, ethyl acetate to afford 156 g of product. The impure fractions were rechromatographed on a high pressure liquid chromatograph (Waters Prep 500 HPLC using 2 silica gel cartridges), eluting with ethyl acetate:methylene chloride, to afford an additional 22 g of product; TLC, $R_f$=0.47, ethyl acetate:methylene chloride (25:75).

h.
(S)-Benzyloxycarbonyl-L-valyl-N-(1-formyl-2-methylpropyl)-L-prolinamide (Formula XI)

A solution of the product of Example 1g (16.97 g) in acetone (800 ml) was added to a solution of concentrated HCl (45 ml) in water (2.6 liter), and the solution was stirred at room temperature for 16 hr. Ethyl acetate was added and the aqueous layer was extracted with ethyl acetate. The organic extracts were dried ($MgSO_4$) and evaporated to afford 12.8 g of yellowish oil: TLC, $R_f$=0.61, ethyl acetate:hexanes (4:1): MS, m/e=432(M+1, base), 199.

h-1. A preferred method for conversion of the acetal product of Example 1g into the aldehyde product of Example 1h is as follows:

To a stirred solution of the acetal product of Example 1g (18.80 g) in acetone (800 ml) under nitrogen was added p-toluenesulfonic acid (360 mg). The mixture was stirred 23 hr and the solvent evaporated. The residue was diluted with ethyl acetate and washed (saturated sodium bicarbonate, brine), dried ($Na_2SO_4$) and evaporated to afford 15.68 g (97%) of the aldehyde product of Example 1h; TLC, $R_f$=0.48, acetone:hexanes (45:55): MS, m/e=460(M+29), 433 (M+2), 432(m+1), 331, 199.

i.
Benzyloxycarbonyl-L-valyl-N-[1-(cyanohydroxymethyl)-2-methylpropyl]-L-prolinamide (Formula XIII, W=CN)

Solid KCN (7.74 g, 119 mmol) was added to a solution of the product of Example 1h, (12.8 g) in tetrahydrofuran(150 ml) and water (128 ml). The resulting mixture was stirred for 4.5 hr, and then partitioned between ethyl acetate and water. The aqueous layer was extracted with ethyl acetate: the combined organic layers were washed with saturated aqueous $NaHCO_3$ and brine, dried (10% (w/w) $K_2CO_3/Na_2SO_4$) and evaporated to afford 14.0 g of crude cyanohydrin: TLC, $R_f$=0.17, acetone:hexanes (1:3).

i-1. An alternative, preferred procedure for preparation of the product of Example 1i is described in Example 4a.

j.
Benzyloxycarbonyl-L-valyl-N-[1-(2-benzoxazolyl)hydroxymethyl-2-methylpropyl]-L-prolinamide (Formula XIV, heterocycle containing X, N and Q=2-benzoxazolyl)

A solution of acetyl chloride (9.50 ml) in ether (15 ml) was added to a solution of absolute ethanol (10.8 ml) in ether (33 ml) at 0° over a period of 20 min. After stirring at 0° for an additional 15 min, the product of Example 1i (used without further purification) (7.70 g) in chloroform (15 ml) was added, and the solution was stirred at 0° for 16 hr. The solvents were evaporated, the residue was dissolved in absolute ethanol (80 ml), and 2-aminophenol (1.83 g) was added. After heating at 60° for 3 hr, the mixture was dissolved in ethyl acetate, washed with 1N NaOH and brine, dried (10% (w/w) $K_2CO_3/Na_2SO_4$), and evaporated. The crude product was flash chromatographed, eluting with acetone:hexanes (3:17), to afford 3 fractions of yellowish foam: fraction one, TLC, $R_f$=0.30, acetone:hexane (3:17), MS, m/e=551(M+1), one isomer, 136 mg: fraction two, TLC, $R_f$=0.25–0.17, acetone:hexane (3:17), all four isomers, 1.77 g: fraction 3, TLC, $R_f$=0.17–0.08, acetone:hexane (3:17), three isomers, 2.45 g.

k.
L-Valyl-N-[1-(2-benzoxazolyl)hydroxymethyl-2-methylpropyl]-L-prolinamide (Formula XV, heterocycle containing X, N and Q=2-benzoxazolyl)

A mixture of 10% palladium on carbon (300 mg, 50% water wet) and the product of Example 1j, fraction three (2.45 g) in ethanol (100 ml) was hydrogenated in a shaker at 3.4 bar for 6 hr after which time an additional amount of palladium on carbon (300 mg) was added and the mixture hydrogenated for an additional 3 hr. The mixture was filtered through diatomaceous earth and the solvent evaporated. The residue was dissolved in ethyl acetate, extracted into 1N HCl and the aqueous acid layer was washed with ethyl acetate, basified with 1N NaOH and, extracted with ethyl acetate. The organic solvent was evaporated to afford 1.40 g (76%) of solid. $R_f$=0.0–0.15, methanol:chloroform (1:19): MS, m/e=471 (M+1), 399.

l.
[4-[(4-Chlorophenyl)sulfonylaminocarbonyl]benzoyl]-L-valyl-N-[1-(2-benzoxazolyl)hydroxymethyl-2-methylpropyl]-L-prolinamide (Formula III, heterocycle containing X, N and Q=2-benzoxazolyl, A=CO, L=p-phenylene, $R^4$=$R^5$.S($O_2$).NH.CO—, $R^5$=4—$ClC_6H_4$).

1-(3-Dimethylaminopropyl)-3-ethylcarbodiimide (710 mg) was added to a solution of the product of Example 1k (1.38g), 1-hydroxybenzotriazole (983 mg) and 4-(4-chlorophenyl)sulfonylaminocarbonyl]benzoic acid (see parts n and o below) (1.12 g) in tetrahydrofuran (18 ml): and the solution was stirred at room temperature for 16 hr. The mixture was partitioned between water and ethyl acetate: the organic phase was washed with 1N HCl and brine, dried (MgSO$_4$), and evaporated. The crude product was purified by flash chromatography, eluting with ethyl acetate:ether:acetic acid (60:40:2 drop/ml), to afford 1.2 g of solid: TLC, R$_f$=0.42, methanol:chloroform:acetic acid (5:95:1 drop/ml): MS, m/e=738(M+1), 421, 318.

Analysis for C$_{36}$H$_{40}$ClN$_5$O$_8$S.1.4 H$_2$O: Calculated: C, 56.64: H, 5.65: N, 9.17. Found: C, 56.97; H, 5.39; N, 8.67.

m. (S)-[4-[(4-Chlorophenyl)sulfonylaminocarbonyl]benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, R$^4$=R5.S(O$_2$).NH.CO—, R$^5$=4—ClC$_6$H$_4$)

Trifluoroacetic acid (0.712 ml) was added to a solution of the product of Example 1, part 1 (1.15 g) and Dess-Martin periodinane (2.65 g) in methylene chloride (15 ml); and the solution was stirred at room temperature for 16 hr. The resulting suspension was partitioned between ethyl acetate and 1N HCl. The organic solution was washed with two portions of 1:1 (w/w) saturated aqueous Na$_2$S$_2$O$_3$: NaHCO$_3$, saturated aqueous NaHCO$_3$ and brine; dried (MgSO$_4$) and evaporated. The crude product was purified by flash chromatography eluting with tetrahydrofuran:methylene chloride:acetic acid (2.5:97.5:1 drop/ml) to afford 889 mg of solid. A second purification was performed using flash chromatography on acidic silica gel, eluting with methanol:chloroform (2.5:97.5), to afford the title compound (701 mg) as a solid: TLC, R$_f$=0.47, ethyl acetate:hexanes:acetic acid (65:35:1 drop/ml): HPLC, t$_R$=9.27, Col B, FR=4, water:acetonitrile:tetrahydrofuran:trifluoroacetic acid (55:35: 15:0.1): MS, m/e=736(M+1), 718, 421, 298.

Analysis for C$_{36}$H$_{38}$ClN$_5$O$_8$S.1.25 H$_2$O: Calculated: C, 56.12; H, 5.47; N, 9.09. Found: C, 56.24: H, 5.07: N, 8.74.

The benzoic acid intermediate used for coupling in part 1. may be prepared as follows:

n. 1,1-Dimethylethyl 4-[(4-chlorophenyl)sulfonylaminocarbonyl]benzoate

A 5-liter 3-neck round bottom flask was equipped with a mechanical stirrer and nitrogen inlet. Methylene chloride (2 liters) was placed in the reaction flask and terephthalic acid mono-t-butyl ester (127.5 g), 4-dimethylaminopyridine (70.06 g), and 4-chlorobenzenesulfonamide (110.04 g) were added sequentially using methylene chloride (400 ml) to wash down the solids. 1-(3-Dimethylaminopropyl)-3-ethylcarbodiimide hydrochloride was added in portions over 10 min using methylene chloride (100 ml) to wash down the solid. After the reaction mixture was stirred overnight at room temperature, it was evaporated to dryness. The residue was partitioned between ethyl acetate and water. The organic solution was washed with 20% (w/v) aqueous citric acid, saturated aqueous NaHCO$_3$ and brine: dried (Na$_2$SO$_4$); and evaporated to a white solid. After drying in a vacuum oven at 50°, the ester (277g, 100%) was obtained in a sufficiently pure state to be used directly for the next step: TLC, R$_f$=0.43, methanol:chloroform (15:85). (Further purification was possible by recrystallization from ethanol/water: mp above 300°).

o. 4-[(4-Chlorophenyl)sulfonylaminocarbonyl]benzoic acid

A 3-liter 3-neck round bottom flask was equipped with a mechanical stirrer and a CaCl$_2$ drying tube. Trifluoroacetic acid (1300 g) was added and cooled to 0°, and the product of Example 1n (79.5 g) was added. Initially, the solid dissolved, giving a clear solution. After 10-15 min, a heavy precipitate of product formed: and it was difficult to stir the reaction mixture. Vigorous stirring with the mechanical stirrer was essential to drive the reaction to completion. The reaction mixture was stirred at 0°-5° for 1 hr before it was poured into 1500 ml of ice/water and stirred for 2 hr. The resulting solid was filtered and dried. The white solid (61.5 g, 91%) obtained was recrystallized from 1600 ml absolute ethanol/1600 ml water to yield the benzoic acid (54 g, 80%) as white needles; mp 286°-288°: TLC, R$_f$=0.7, methanol:chloroform:acetic acid (10:90:1).

EXAMPLE 2

[4-(Methylsulfonylaminocarbonyl)benzoyl]-L-valyl-N-]1-(2-benzoxazolyl)carbonyl-2-methylpropyl]-L-prolinamide (Formula I, heterocycle containing X, N and Q=2-benzoxazolyl, A=CO, L=p-phenylene, R$^4$=R$^5$.S(O$_2$).NH.CO—, R$^5$=CH$_3$)

a. (1S)-[4-(1,1-Dimethylethoxy)carbonylbenzoyl]-L-valyl-N-[1-(2-benzoxazolyl)hydroxymethyl-2-methylpropyl]-L-prolinamide (Formula XVII, heterocycle containing X, N and Q=2-benzoxazolyl, R$^7$.L.A=4-[(CH$_3$)$_3$COCO C$_6$H$_4$CO)

1-(3-Dimethylaminopropyl)-3-ethylcarbodiimide hydrochloride (510 mg) was added to a solution of product prepared by the method of Example 1k [material prepared according to the method of Example 1j and obtained in the (1S)-form was treated according to the procedure of Example 1k and obtained in the (1S)-form](1.00 g), 1-hydroxybenzotriazole (720 mg), and terepthalic acid mono-t-butyl ester (560 mg) in tetrahydrofuran(5 ml) at 0° : and the solution was allowed to warm to room temperature and stirred for 16 hr. The mixture was partitioned between water and ethyl acetate, the organic phase was washed with 1N HCl (twice), saturated sodium bicarbonate (twice) and brine, dried (MgSO$_4$) and evaporated. The crude product was purified by flash chromatography, eluting with acetone:hexane (4:6), to afford the product (1.08 g, 73%) as a solid: TLC, R$_f$=0.7, acetone:hexane (45:55): MS, m/e=621 (M+1), 649, 622, 565, 318.

Analysis for C$_{34}$H$_{44}$N$_4$O$_4$.0.4 H$_2$O: Calculated: C, 65.03: H, 7.19; N, 8.92. Found: C, 65.06: H, 7.05: N, 8.72.

b. (S)-[4-(1,1-Dimethylethoxy)carbonylbenzoyl]-L-valyl-N-[1-(2-benzoxazolyl)carbonyl-2-methylpropyl]-L-prolinamide (Formula IV, heterocycle containing X, N and Q=2-benzoxazolyl, R$^7$.L.A=4-[(CH$_3$)$_3$COCO]C$_6$H$_4$CO).

t-Butyl alcohol (0.030 ml) was added to a solution of the product of Example 3a (200 mg) and Dess-Martin periodinane (410 mg) in methylene chloride (5 ml) and the solution stirred at room temperature for 16 hr. The resulting solution was partitioned between ethyl acetate and 1:1 saturated Na$_2$S$_2$O$_3$:NaHCO$_3$. The organic phase was separated and washed with 1:1 saturated Na$_2$S$_2$O$_3$: NaHCO$_3$ (twice) and brine, dried [K$_2$CO$_3$:Na$_2$SO$_4$(1:2, w:w)] and evaporated. The crude product was purified by flash chromatography, eluting with acetone:hexanes (1:3) to afford the product (161 mg, 80%) as a solid: TLC, $R_f=0.35$, acetone:hexanes (1:3): HPLC, $t_R=7.86$, Col A, FR=2, water:acetonitrile (40:60): MS, m/e=619 (M+1), 563, 316, 304, 204, 120, 115.

Analysis for $C_{34}H_{42}N_4O_7.0.4\ H_2O$: Calculated: C, 65.24: H, 6.89; N, 8.95. Found: C, 65.26; H, 6.74: N, 8.84.

c.
(4-Carboxybenzoyl)-L-valyl-N-[1-(2-benzoxazolyl)carbonyl-2-methylpropyl]-L-prolinamide (Formula IV, heterocycle containing X, N and Q=2-benzoxazolyl, $R^7.L.A=4—(HOOC)C_6H_4CO$).

A solution of the product of Example 3b (770 mg) in trifluoroacetic acid (5 ml) was stirred at room temperature for 2 hr. The solvent was then evaporated. The residual oil was diluted with ether and the resulting solution was evaporated. This process was repeated 6 times. The brown oil was then placed under high vacuum for 48 hr. The crude acid (now a foam) was purified by flash chromatography, eluting with acetone:hexane:acetic acid (40:60:1) to afford the product (680 mg, 96%) as a yellow solid; TLC, $R_f=0.23$, acetone:hexanes:acetic acid (4:6:1 drop/ml): MS, m/e=563 (M+1), 545, 316, 298, 248, 245, 220, 204, 149, 148, 120.

Analysis for $C_{30}H_{34}N_4O_7.0.2\ NaOH.0.55\ H_2O$: Calculated: C, 62.07: H, 6.13; N, 9.65. Found: C, 61.70, H, 5.95: N, 9.92.

d.
[4-(Methylsufonylaminocarbonyl)benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, $R^4=R^5.S(O_2).NH.CO—$, $R^5=CH_3$)

1-(3-Dimethylaminopropyl)-3-ethylcarbodiimide hydrochloride (78 mg) was added to a solution of the product of Example 3c (200 mg), 4-dimethylaminopyridine (58 mg), and methanesulfonamide (37 mg) in methylene chloride (2 ml), and the solution stirred at room temperature for 16 hr. After the solvents were evaporated, the residue was partitioned between ethyl acetate and 1N HCl. The organic layer was separated, washed with 1N HCl, dried (MgSO4) and evaporated. The crude product was purified by flash chromatography, eluting with ethyl acetate:ether:acetic acid (20:80:1) to afford the product (74.2 mg, 32%) as a solid: TLC, $R_f=0.10$, ether:acetic acid (100:1): HPLC, t 03, Col B, FR=2, water:acetonitrile:tetrahydrofuran: trifluoroaceic acid (55:35:13:0.1); MS, m/e=640 (M+1), 622, 326, 325, 316, 298, 247, 201.

Analysis for $C_{31}H_{37}N_5O_8S.0.8\ CH_3CO_2H$: Calculated: C, 56.93: H, 5.89; N, 10.18. Found: C, 57.22: H, 5.97: N, 9.79.

EXAMPLE 3

(S)-[4-(Phenylsulfonylaminocarbonyl)benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, $R^4=R^5.S(O_2).NH.CO—$, $R^5=C_6H_5$)

a. 4-(Phenylsulfonylaminocarbonyl)benzoic acid

Using similar procedures to those described in Example 1 parts n and o, except using benzenesulfonamide in place of 4-chlorobenzenesulfonamide, the benzoic acid was obtained as a solid; mp 259°-261°.

b.
(1S)-[4-(Phenylsulfonylaminocarbonyl)benzoyl]-L-valyl-N-[1-(2-benzoxazolyl)hydroxymethyl-2-methylpropyl]-L-prolinamide (Formula III, heterocycle containing X, N and Q=2-benzoxazolyl, A=CO, L=p-phenylene, $R^4=R^5.S(O_2).NH.CO—$, $R^5=C_6H_5$)

1-(3-Dimethylaminopropyl)-3-ethylcarbodiimide hydrochloride (140 mg) was added to a solution of the product of Example 1k (290 mg), 1-hydroxybenzotriazole (200 mg), and 4-(phenylsulfonylaminocarbonyl)benzoic acid (179 mg) in tetrahydrofuran (4 ml): and the solution stirred at room temperature for 16 hr. The mixture was partitioned between water and ethyl acetate. The organic phase was washed with saturated NaHCO3 (3 times) and brine, dried (MgSO4) and evaporated. The aqueous layers were combined, acidified to pH 1 with concentrated HCl, and extracted with chloroform. The chloroform phase was dried [$K_2CO_3:Na_2SO_4$ (1:2, w:w)] and evaporated. The crude product obtained from both the ethyl acetate and chloroform solutions was combined and purified by flash chromatography, eluting with acetone:hexanes: acetic acid (45:55:1), to afford the product (270 mg, 60%) as a solid: $R_f=0.15$, acetone:hexane:acetic acid (30:70:1 drop/ml): MS, m/e=704 (M+1), 686, 387, 346, 318, 316, 300, 158, 120.

Analysis for $C_{36}H_{41}N_5O_8S.0.8\ CH_3CO_2H$: Calculated: C, 58.79; H, 6.03; N, 9.07. Found: C, 59.11: H, 6.02: N, 8.68.

c.
(S)-[4-(Phenylsulfonylaminocarbonyl)benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, $R^4=R^5.S(O_2).NH.CO—$, $R^5=C_6H_5$)

Trifluoroacetic acid (0.09 ml) was added to a solution of the product of Example 4b (270 mg) and Dess-Martin periodinane (490 mg) in methylene chloride (5 ml) and the solution stirred at room temperature for 16 hr. The resulting solution was diluted with ethyl acetate and washed (4 times with 4:1 brine:saturated $Na_2S_2O_3:Na_2HCO_3$ (1:1), once with brine), dried (MgSO4) and evaporated. The crude product was purified by flash chromatography, eluting with acetone:hexanes:acetic acid (40:60:1). The solid obtained from this column was further purified by flash chromatography on acidic silica gel eluting with chloroform to afford the title compound (152 mg, 57%) as a solid: TLC, R =0.23, acetone:hexanes:acetic acid (40:60:1): HPLC, $t_R=10.09$, Col B, FR=2, water: acetonitrile:tetrahydrofuran:trifluoracetic acid (55:35:15:0.1): MS, m/e=702 (M+1), 326, 299, 298, 297, 201, 136.

Analysis for $C_{36}H_{39}N_5O_8S.0.75\ NaOH.0.25\ H_2O$: Calculated: C,58.72; H,5.51; N,9.51. Found: C,58.38: H,5.34: N,9.28.

EXAMPLE 4

(S)-[4-[(4-Chlorophenyl)sulfonylaminocarbonyl]benzoyl[-L-valyl-N-[1-(5-methoxybenzoxazol-2-yl)carbonyl-2-methylpropyl]-L-prolinamide (Formula I, heterocycle containing X, N and Q=5-methoxybenzoxazol-2-yl, A=CO, L=p-phenylene, $R^4=R^5.S(O_2).NH.CO-$, $R^5=4-ClC_6H_4$)

a.
(1S)-Benzyloxycarbonyl-L-valyl-N-[1-(cyanohydroxymethyl)-2-methylpropyl]-L-prolinamide (Formula XIII, W=CN)

An alternative, preferred procedure for preparation of the product of Example 1i is as follows: A 250 ml round bottom flask with stirrer was dried under vacuum and purged with nitrogen. The flask was charged with dichloromethane (120 ml) followed by the addition of aldehyde prepared as described in Example 1h (17.7 g) and triethyl amine (3.4 ml). Acetone cyanohydrin (11.0 ml) was added in one portion. The reaction mixture was stirred for 21 hr. The crude reaction mixture was diluted with dichloromethane. This solution was carefully washed (twice with saturated ammonium chloride, once with brine), dried (MgSO$_4$), and the solvent evaporated. The crude product was dissolved in ethyl acetate, washed (once with saturated ammonium chloride, once with brine), dried (MgSO$_4$), and evaporated. The resulting foam was heated to 50° under vacuum for four days to afford 18.90 g (100%) of product: TLC, $R_f=0.31$, acetone:hexanes (40:60).

b.
(1S)-Benzyloxycarbonyl-L-valyl-N-[3-ethoxy-2-hydroxy-3-imino-1-(1-methylethyl)propyl]-L-prolinamide hydrochloride (Formula XIII, W=C(NH)OR, R=C$_2$H$_5$)

To a stirred solution of ethanol (79.4 ml) in chloroform (80 ml) at 0° under nitrogen was added dropwise acetyl chloride (87.7 ml) over the course of 25 min. The product of Example 4a (18.81 g) in chloroform (80 ml) was added and the reaction stirred at 0° for 4 hr. The solvents were evaporated to afford the product (20.89 g); TLC, after partitioning an aliquot between ethyl acetate and 1N NaOH to form the free imino ether, $R_f=0.45$, methanol:chloroform (7.5:92.5).

c. 2-Amino-4-methoxyphenol

A mixture of 10% (w/w) palladium on carbon (200 mg) and 4-methoxy-2-nitrophenol (3.0 g) in ethanol (100 ml) was hydrogenated in a shaker at 3.4 bar for 24 hr. The mixture was filtered through diatomaceous earth and evaporated to give the product (2.3 g): TLC, $R_f=0.61$, methanol:chloroform (1:9): MS, m/e=170(M+1), 164, 152(base), 124.

d.
(1S)-Benzyloxycarbonyl-L-valyl-N-[1-(hydroxy)-(5-methoxybenzoxazol-2-yl)methyl-2-methylpropyl]-L-prolinamide (Formula XIV, heterocyle containing X, N and Q=5-methoxybenzoxazol-2-yl)

A stirred solution of the imidate of Example 4b (6.35 g) and 2-amino-4-methoxyphenol (1.525 g) in dry ethanol (40 ml) was heated for 8 hr at 60° under nitrogen. The mixture was dissolved in ethyl acetate, washed (1N HCl, saturated sodium bicarbonate, brine), dried (10% (w/w) K$_2$CO$_3$/Na$_2$SO$_4$), and evaporated. The crude product was flash chromatographed eluting with acetone:hexanes (30:70) to afford the product (983 mg). The mixed fractions were combined, evaporated and flash chromatographed eluting with acetone:hexanes (35:65) to afford additional product (588 mg): TLC, $R_f=0.28$, acetone:hexanes (40:60): MS, m/e=582(M+2), 581(M+1), 563, 473, 331, 261, 195, 107, 91, 79, 70.

e.
(1S)-L-Valyl-N-[1-(hydroxy)(5-methoxybenzoxazol-2-yl)methyl-2-methylpropyl]-L-prolinamide (Formula XV, heterocycle containing X, N and Q=5-methoxybenzoxazol-2-yl)

A mixture of 10% (w/w) palladium on carbon (300 mg) and the product from Example 4d (1.54 g) in ethanol (100 ml) was hydrogenated in a shaker at 3.4 bar for 4 hr, after which time the mixture was filtered through diatomaceous earth and the solvent evaporated. The residue was redissolved in ethanol (100 ml), 10% palladium on carbon (0.69 g) added and the mixture hydrogenated in a shaker at 3.4 bar for 4 hr. The mixture was then filtered through diatomaceous earth and the solvent evaporated to afford 990 mg (83%) of solid: $R_f=0.0$, methanol:chloroform (1:19): MS, m/e=475(M+29), 447(M+1), 429, 348, 234, 233, 197, 180, 179, 178, 155, 150, 100, 72, 70.

f.
(1S)-[4-[(4-Chlorophenyl)sulfonylaminocarbonyl]benzoyl]-L-valyl-N-[1-(hydroxy)(5-methoxybenzoxazol-2-yl)methyl-2-methylpropyl]-L-prolinamide (Formula III, heterocycle containing X, N and Q=5-methoxybenzoxazol-2-yl, A=CO, L=p-phenylene, $R^4=R^5.S(O_2).NH.CO-$, $R^5=4-ClC_6H_4$)

1-(3-Dimethylaminopropyl)-3-ethylcarbodiimide hydrochloride (470 mg) was added to a solution of the product of Example 4e (990 mg), 1-hydroxybenzotriazole (330 mg), and the product of Example 1 part o (830 mg) in tetrahydrofuran (7 ml); and the solution was stirred at room temperature for 16 hr. The reaction mixture was then stored at −78° for 36 hr. The reaction mixture was diluted with ethyl acetate, washed (saturated sodium bicarbonate, 1N HCl, brine), dried (Na$_2$SO$_4$), and evaporated. The resulting solid was redissolved in ethyl acetate, washed (saturated sodium bicarbonate, 1N HCl, brine), dried (Na$_2$SO$_4$), and evaporated. The crude product was purified by flash chromatography eluting with acetone:chloroform:acetic acid (20:80:1) to afford the product (976 mg) as a solid; TLC, $R_f=0.25$, acetone:chloroform:acetic acid (35:65:1): MS, m/e=768(M+1), 752, 751, 750, 423, 422, 421, 402, 377, 348, 330.

Analysis for C$_{37}$H$_{42}$ClN$_5$O$_9$S.1.8 CH$_3$CO$_2$H: Calculated: C, 55.97: H, 5.63; N, 8.16. Found: C, 56.14: H, 5.76; N, 7.95.

g.
(S)-[4-[(4-Chlorophenyl)sulfonylaminocarbonyl]benzoyl]-L-valyl-N-[1-(5-methoxybenzoxazol-2-yl)carbonyl-2-methylpropyl]-L-prolinamide (Formula I, heterocycle containing X, N and Q=5-methoxybenzoxazol-2-yl, A=CO, L=p-phenylene, $R^4=R^5.S(O_2).NH.CO-$, $R^5=4-ClC_6H_4$)

t-Butanol (0.116 ml) was added to a solution of the product of Example 4f (947.6 mg) and Dess-Martin periodinane (1.57 g) in dichloromethane (6 ml), and the solution stirred at room temperature for 21 hr. The resulting suspension was diluted with ethyl acetate and washed (twice with 1:1 saturated $Na_2S_2O_3$: saturated $NaHCO_3$, once with 1N HCl, brine), dried ($MgSO_4$) and evaporated. The crude product was purified by flash chromatography eluting with acetone:hexane:acetic acid (50:50:1) to afford the product (703 mg) as a solid: TLC, $R_f$=0.47, ethyl acetate:hexanes:acetic acid (65:35:1) MS, m/e=766(M+1), 750, 749, 748, 422, 421, 329, 328, 327, 326, 249, 231.

Analysis for $C_{37}H_{38}ClN_5O_9S.1.1\ H_2O.1.1\ CH_3CO_2H$: Calculated: C, 55.26: H, 5.51; N, 8.22. Found: C, 55.16: H, 5.20: N, 8.08.

EXAMPLE 5

(S)-[4-[(4-Chlorophenyl)sulfonylaminocarbonyl]benzoyl]-L-valyl-N-[1-(5-hydroxybenzoxazol-2-yl)carbonyl2-methylpropyl]-L-prolinamide (Formula I, heterocycle containing X, N and
Q=5-hydroxybenzoxazol-2-yl, A=CO,
L=p-phenylene, $R^4=R^5.S(O_2).NH.CO—$,
$R^5=4—ClC_6H_4$)

Boron tribromide (3.55 ml, 1.0M in dichloromethane) was added to a solution of the product of Example 4g (680 mg) in dichloromethane (5 ml) at 0° and allowed to warm to room temperature. After 3 hours, the reaction mixture was partitioned between ethyl acetate and 1N HCl. The ethyl acetate layer was washed (brine), dried ($MgSO_4$), and evaporated. The crude product was purified by flash chromatography eluting with methanol:chloroform:acetic acid (1:98:1) to give the product (236 mg, 35%) as a yellow solid: TLC, $R_f$=0.28, methanol:chloroform:acetic acid (5:94:1); HPLC, $t_R$=6.75, Col A, FR=3, water:acetonitrile:tetrahydrofuran:trifluoroacetic acid (55:35:15:0.1); MS, m/e=752(M+1), 734, 421, 377, 342, 314(base).

Analysis for: $C_{36}H_{38}ClN_5O_9S.0.2\ CHCl_3.030\ CH_3COOH.1.5\ H_2O$: Calculated: C, 53.83; H, 5.20: N, 8.53. Found: C, 53.65: H, 4.96; N, 8.37.

EXAMPLE 6

[4-[(4-Chlorophenyl)sulfonylaminocarbonyl]benzoyl]-L-valyl-N-[1-[5-(aminocarbonyl)benzoxazol-2-yl)carbonyl-2-methylpropyl]-L-prolinamide (Formula I, heterocycle containing X, N and
Q=5-(aminocarbonyl)benzoxazol-2-yl, A=CO,
L=p-phenylene, $R^4=R^5.S(O_2).NH.CO—$,
$R^5=4-ClC_6H_4$)

a. 3-Amino-4-hydroxybenzamide

A solution of 3-amino-4-hydroxybenzoic acid (7.73 g) in thionyl chloride (96 ml) was stirred vigorously under nitrogen at 40° for one hour. The thionyl chloride was removed by distillation under reduced pressure and the resulting solid was suspended in toluene (350 ml). Anhydrous $NH_3$ was bubbled into the reaction mixture for 45 minutes. The mixture was filtered through diatomaceous earth and the filter cake was washed copiously with acetone until fresh filtrate was clear. The acetone solution was evaporated, and the crude product was flash chromatographed eluting with acetone:choloroform (1:1) to afford the product (1.2 g) as a solid: TLC, $R_f$=0.17 acetone:chloroform (60:40); MS, m/e=193(M+41), 181(M+29), 153(M+1), 136, 110.

b.

(1S)-Benzyloxycarbonyl-L-valyl-N-[1-[5-aminocarbonyl)benzoxazol-Z-yl]hydroxymethyl-2-methylpropyl]-L-prolinamide (Formula XIV, heterocycle containing X, N and
Q=5-(aminocarbonyl)benzoxazol-2yl)

A stirred solution of the imidate of Example 4b (3.81 g) and 3-amino-4-hydroxybenzamide (1.00 g) in dry ethanol (28 ml) was heated for 2 hr at 60° under nitrogen The mixture was dissolved in ethyl acetate, washed (twice with water, once with saturated sodium bicarbonate, brine), dried ($MgSO_4$), and evaporated. The crude product was flash chromatographed eluting with acetone:chloroform (60:40) to afford the product (936 mg); TLC, $R_f$=0.42, tetrahydrofuran:chloroform (75:25); MS, m/e=622(M+29), 595(M+2), 594(M+1), 505, 478, 477.

Analysis for $C_{31}H_{39}N_5O_7.2.0\ H_2O$: Calculated: C, 59.13; H, 6.88: N, 11.12. Found: C, 59.18: H, 6.35; N, 11.04.

c.

(1S)-L-Valyl-N-[1-[5-(aminocarbonyl)benzoxazol-2-yl]hydroxymethyl-2-methylpropyl]-L-prolinamide (Formula XV, heterocycle containing X, N and
Q=5-(aminocarbonyl)benzoxazol-2-yl)

A mixture of 10% (w/w) palladium on carbon (750 mg) and the product from Example 6b (0.920 g) in ethanol (150 ml) was hydrogenated in a shaker at 3.4 bar for 4 hr after which time the mixture was filtered through diatomaceous earth and the solvent evaporated. The residue was then redissolved in methanol and evaporated to afford the product (680 mg, 100%) as a solid: TLC $R_f$=0.0, methanol:chloroform (5:95): MS, m/e=460(M+1), 247, 225, 198, 197, 196, 154, 125, 91.

d.

(1S)-[4-[(4-Chlorophenyl)sulfonylaminocarbonyl]benzoyl]-L-valyl-N-[1-[5-(aminocarbonyl)benzoxazol-2-yl]hydroxymethyl-2-methylpropyl]-L-prolinamide (Formula III, heterocycle containing X, N and
Q=5-(aminocarbonyl)benzoxazol-2-yl, A=CO,
L=p-phenylene, $R^4=R^5.S(O_2).NH.CO—$,
$R^5=4—ClC_6H_4$)

1-(3-Dimethylaminopropyl)-3-ethylcarbodiimide hydrochloride (292 mg) was added to a solution of the product of Example 6c (670 mg), 1-hydroxybenzotriazole (206 mg), and the product of Example 1-part o (507 mg) in tetrahydrofuran (5 ml): and the solution stirred at room temperature for 16 hr. The reaction mixture was diluted with ethyl acetate and washed three times with distilled water, once with 1N HCl, once with saturated sodium bicarbonate, and once with brine. The bicarbonate wash was acidified to pH 1 and extracted three times with ethyl acetate. The combined organic phases were washed with brine, dried ($Na_2SO_4$), and evaporated. The crude product was flash chromatographed eluting with tetrahydrofuran:chloroform:acetic acid (70:30:1). The resulting material was filtered through silica gel eluting with tetrahydrofuran:chloroform:acetic acid (30:70:0 to 30:70:1 to 100:0:1) to afford the product (350 mg) as a solid: TLC, $R_f$=0.55, tetrahydrofuran:chloroform:acetic acid (80:20:1): MS, m/e=247, 197, 163.

e.
[4-[(4-Chlorophenyl)sulfonylaminocarbonyl]benzoyl]-L-valyl-N-1-(5-(aminocarbonyl)benzoxazol-2-yl)carbonyl-2-methylpropyl]-L-prolinamide (Formula I, heterocycle containing X, N and Q=5-(aminocarbonyl)benzoxazol-2-yl, A=CO, L=p-phenylene, $R^4=R^5.S(O_2).NH.CO—$, $R^5=4—ClC_6H_4$)

Pyridine (0.422 ml) was added to a suspension of chromium trioxide (261 mg) in dry dichloromethane (27 ml), and the mixture stirred at room temperature 30 min. Diatomaceous earth (0.5 g) was added to the mixture which was stirred 5 more min. The product from Example 6d (340 mg) in dry dimethylformamide (1.5 ml) was added, and the mixture and was allowed to stir for 3.5 hr. The resulting suspension was filtered through diatomaceous earth and evaporated. The residue was lixiviated with chloroform and filtered through diatomaceous earth. (The use of methanol for lixiviation is preferred.) This process was repeated six times. The filtrates were combined and evaporated. The resulting solid was flash chromatographed eluting with tetrahydrofuran:chloroform:acetic acid (55:45:1). The resulting solid was filtered through silica gel, eluting first with chloroform then with tetrahydrofuran:acetic acid (99:1). The resulting solid was again flash chromatographed eluting with tetrahydrofuran:hexanes:acetic acid (60:40:1) to afford the product (37.5 mg); TLC, $R_f=0.50$, methanol:chloroform:acetic acid (10:90:1): HPLC, $t_R=23$, Col A, FR=1, water:acetonitrile:tetrahydrofuran:trifluoroacetic acid (55:35:15:0.1): MS, m/e=777(M+1), 761, 421, 342, 341, 340, 339, 192.

Analysis for $C_{37}H_{39}ClN_6O_9S.0.90$ $H_2O.1.0$ $CH_3CO_2H$: Calculated: C, 54.75: H, 5.28: N, 9.82. Found: C, 55.07: H, 5.41: N, 9.57.

EXAMPLE 7

[4-[(4-Chlorophenyl)sulfonylaminocarbonyl]benzoyl]-L-valyl-N-[1-[5-(hydroxymethyl)benzoxazol-2-yl]carbonyl-2-methylpropyl]-L-prolinamide (Formula I, heterocycle containing X, N and Q=5-(hydroxymethyl)benzoxazol-2-yl, A=CO, L=p-phenylene, $R^4=R^5.S(O_2).—NH.CO—$, $R^5=4—ClC^6H^4$)

a. 3-Amino-4-hydroxybenzyl alcohol

A mixture of 10% (w/w) palladium on carbon (5.25 g) and 4-hydroxy-3-nitrobenzyl alcohol (25.0 g) in ethanol (1.3 liter) was hydrogenated in a shaker at 3.4 bar for 23 hr, after which time the mixture was filtered through diatomaceous earth and evaporated. The residue was flash chromatographed, eluting with methanol:chloroform (0:100 to 10:90), to afford the product (11.92 g, 60%) as a red solid; TLC, $R_f=0.14$, methanol:chloroform (5:95): MS, m/e=140(M+1), 139, 138, 123, 122, 110.

b.
(1S)-Benzyloxycarbonyl-L-valyl-N-[1-(hydroxy)[5-(hydroxymethyl)benzoxazol-2-yl]methyl-2-methylpropyl]-L-prolinamide (Formula XIV, heterocycle containing X, N, and Q=5-(hydroxymethyl)benzoxazol-2-yl)

The product from Example 4b (3.0 g) and alcohol prepared according to Example 7a (0.771 g) in absolute ethanol (20 ml) were heated at 65° for 20 hr: the mixture was dissolved in ethyl acetate, washed (1N NaOH, brine), dried (MgSO₄), and evaporated. The crude product was flash chromatographed eluting with acetone:hexanes (55:45) to give the product (858 mg) as a white solid: TLC, $R_f=0.26$, acetone:hexanes (3:2): MS, m/e=581(M+1), 563, 501, 473, 455.

Analysis for $C_{31}H_{40}N_4O_7.1.25$ $H_2O$: Calculated: C, 61.73; H, 7.10; N, 9.29. Found: C, 61.81: H, 6.86; N, 9.09.

c.
(1S)-Benzyloxycarbonyl-L-valyl-N-[1-[5-[(t-butyldimethylsilyloxy)methyl]benzoxazol-2-yl]-(hydroxy)methyl-2-methylpropyl]-L-prolinamide (Formula XIV, heterocycle containing X, N and Q=5-[(t-butyldimethylsilyloxy)methyl]benzoxazol-2-yl)

A solution of the product of Example 7b (736 mg), t-butyldimethylsilyl chloride (380 mg), 4-dimethylaminopyridine (7.8 mg), and triethylamine (0.37 ml) in dichloromethane (10 ml) was stirred at room temperature for 16 hr. The solution was then dissolved in ethyl acetate, washed (1N HCl, saturated sodium bicarbonate, brine), dried (MgSO₄), and evaporated. The crude product was purified by flash chromatography, eluting with acetone:hexanes (1:3), to afford the product (715 mg, 82%) as a light yellow solid; TLC, $R_f=0.46$, acetone:hexanes (2:3): MS, m/e=695(M+1), 679, 587, 563, 455.

Analysis for $C_{37}H_{54}N_4O_7Si.0.25$ $H_2O$: Calculated: C, 63.54: H, 7.85; N, 8.01. Found: C, 63.44: H, 7.75; N, 7.54.

d.
(S)-Benzyloxycarbonyl-L-valyl-N-[1-[5-[(t-butyldimethylsilyloxy)methyl]benzoxazol-2-yl]carbonyl-2-methylpropyl]-L-prolinamide (Formula VI, heterocycle containing X, N and Q=5-[(t-butyldimethylsilyloxy)methyl]benzoxazol-2-yl)

Tert-butyl alcohol (0.068 ml) was added to a solution of the product of Example 7c (500 mg) and Dess-Martin periodinane (1.22 g) in dichloromethane (5 ml) and the solution stirred at room temperature for 16 751 hr. The resulting suspension was partitioned 90%) between ethyl acetate and a 1:1 solution of saturated $Na_2S_2O_3$:saturated $NaHCO_3$; the layers were separated; and the ethyl acetate layer washed (once with a 1:1 solution of saturated $Na_2S_2O_3$:saturated $NaHCO_3$, twice with saturated $NaHCO_3$, once with brine), dried (MgSO₄), and evaporated. The crude product was purified by flash chromatography eluting with acetone:hexanes (1:3) to afford the product (448 mg, as a white solid: TLC, $R_f=0.54$, acetone:hexanes (2:3): HPLC, $t_R=6.18$, Col A, FR=2, water:acetonitrile (1:9): MS, m/e=603(M+1, base), 677, 635, 585, 460.

Analysis for $C_{37}H_{52}N_4O_7Si.0.25$ $H_2O$: Calculated: C, 63.72: H, 7.59; N, 8.03. Found: C, 63.84: H, 7.45: N, 7.70.

e.
Benzyloxycarbonyl-L-valyl-N-[1-[5-(hydroxymethyl)benzoxazol-2-yl]carbonyl-2-methylpropyl]-L-prolinamide (Formula VI, heterocycle containing X, N and Q=5-(hydroxymethyl)benzoxazol-2-yl).

Tetrabutylammonium fluoride (1.2 ml of 1M solution in tetrahydrofuran) was added to a solution of the product of Example 7d (418 mg) in tetrahydrofuran (5 ml). The resulting red solution was stirred at room temperature for 10 min and stored at 5° for 16 hr. The red solution was partitioned between ethyl acetate and 1N HCl, and the ethyl acetate layer was washed (saturated sodium bicarbonate, brine), dried (MgSO₄), and evaporated. The crude product was purified by flash chromatography eluting with acetone:hexanes (35:65) followed by a second purification by flash chromatography eluting with methanol:chloroform (2.5:97.5) to afford the product (183 mg, 53%) as a white solid: TLC, $R_f$=0.52, acetone:hexanes (3:2): HPLC, $t_R$=6.27, Col A, FR=1, water:acetonitrile (40:60): MS, m/e=579(M+1), 561, 331, 225, 197, 91(base).

Analysis for $C_{31}H_{38}N_4O_7 \cdot 1.0\ H_2O$: Calculated: C, 62.40: H, 6.76; N, 9.39. Found: C, 62.23; H, 6.40; N, 9.14.

f.

[4-[(4-Chlorophenyl)sulfonylaminocarbonyl]benzoyl]-L-valyl-N-[1-[5-(hydroxymethyl)benzoxazol-2-yl]carbonyl-2-methylpropyl]-L-prolinamide (Formula I, heterocycle containing X, N and Q=5-(hydroxymethyl)benzoxazol-2-yl, A=CO, L=p-phenylene, $R^4$=$R^5.S(O_2)$.—NH.CO—, $R^5$=r—$ClC_6H_4$)

Trifluoromethanesulfonic acid (0.140 ml) was added to a solution of material prepared according to the procedure of Example 7e (182 mg) in dichloromethane (8 ml), stirred for 15 min, and evaporated. The residue was dissolved in tetrahydrofuran (10 ml) and treated with 4-dimethylaminopyridine (293 mg), the product of Example 1 part o (113 mg), and 1-(3-dimethylaminopropyl)-3-ethyl carbodiimide hydrochloride (66.5 mg), and stirred at room temperature for 16 hr. The mixture was partitioned between 1N HCl and ethyl acetate; the ethyl acetate phase was washed (1N HCl, brine), dried ($MgSO_4$), and evaporated. The crude product was purified by flash chromatography eluting with methanol:chloroform:acetic acid (1.5:97.5:1.0) to afford the product (77 mg, 32%) as a light yellow solid: TLC, Rf=0.28, methanol:chloroform:acetic acid (5:94:1): MS, m/e=766(M+1), 758, 592, 562, 421, 346, 328.

Analysis for $C_{37}H_{40}ClN_5O_9S \cdot 1.0\ H_2O \cdot 1.0\ CH_3COOH$:
Calculated: C, 55.48: H, 5.49; N, 8.29.
Found: C, 55.42: H, 5.33: N, 8.77.

EXAMPLE 8

(S)-[4-[(4-Chlorophenyl)sulfonylaminocarbonyl]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4$=$R^5.S(O_2).NH.$—CO—, $R^5$=4—$ClC_6H_4$)

a.

(1S)-Benzyloxycarbonyl-L-valyl-N-[1-(hydroxy)-[5-(methoxycarbonyl)benzoxazol-2-yl]methyl-2-methylpropyl]-L-prolinamide (Formula XIV, heterocycle containing X, N and Q=5-(methoxycarbonyl)benzoxazol-2-yl)

A stirred solution of the imidate of Example 4b (5.47 g) and 4-carbomethoxy-2-aminophenol (5.10 g) in dry ethanol (50 ml) was heated for 3 hr at 60° under nitrogen. The mixture was dissolved in ethyl acetate, washed (1N HCl, 1N NaOH three times, brine), dried ($MgSO_4$), and evaporated. The crude product was flash chromatographed, eluting with acetone:hexanes (30:70), to afford 2.210 g of the product TLC, $R_f$=0.18, acetone:hexanes (35:65); MS, 649(M+41), 637(M+29), 611(M+3), 610(M+2), 609(M+1), 591, 501.

Analysis for $C_{32}H_{40}N_4O_8 \cdot 0.35\ CH_3CO_2C_2H_5$:
Calculated: C, 62.73; H, 6.74; N, 8.76
Found: C, 62.71: H, 6.73; N, 8.67 b.

(S)-Benzyloxycarbonyl-L-valyl-N-[1-[5-(methoxycarbonyl)benzoxazol-2-yl]carbonyl-2-methylpropyl]-L-prolinamide (Formula VI, heterocycle containing X, N and Q=5-(methoxycarbonyl)benzoxazol-2-yl)

t-Butanol (0.340 ml) was added to a solution of the product of Example 8a (2.70 g) and Dess-Martin periodinane (4.62 g) in dichloromethane (20 ml) and the solution stirred at room temperature for 22 hr. The resulting suspension was diluted with ethyl acetate and was washed (three portions of 1:1 saturated $Na_2S_2O_3$:-saturated $NaHCO_3$, brine), dried ($MgSO_4$), and evaporated. The crude product was purified by flash chromatography eluting with acetone:hexane (25:75) to afford 2.20 g of solid: TLC, $R_f$=0.21, acetone:hexanes (30:70); MS, m/e=635(M+29), 608(M+2), 607(M+1), 374, 331, 91.

Analysis for $C_{32}H_{38}N_4O_8 \cdot 0.50\ H_2O$:
Calculated: C, 62.43; H, 6.38: N, 9.10.
Found: C, 62.43: H, 6.24: N, 8.91.

c.

(S)-L-Valyl-N-[1-[5-(methoxycarbonyl)benzoxazol-2-yl]carbonyl-2-methylpropyl]-L-prolinamide (Formula V, heterocycle containing X, N and Q=5-(methoxycarbonyl)benzoxazol-2-yl)

To a stirred solution of the product of Example 8b (500 mg) in dichloromethane (4 ml) under nitrogen was added trifluoromethanesulfonic acid (0.365 ml) dropwise. After 5 min the reaction mixture was poured into distilled water (100 ml) and was extracted three times with dichloromethane. The aqueous layer was adjusted to pH 8 with $NaHCO_3$ and washed three times with dichloromethane. The aqueous phase was treated with 1N NaOH (50 ml) and washed once more with dichloromethane. The organic washes were combined, dried ($Na_2SO_4$), and evaporated to afford 185 mg (48%) of a white foam: TLC, Rf=0.22, methanol:chloroform (5:95).

d.

(S)-[4-[(4-Chlorophenyl)sulfonylaminocarbonyl]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4$=$R^5.S(O_2).NH.CO$—, $R^5$=4—$ClC_6H_4$)

1-(3-Dimethylaminopropyl)-3-ethylcarbodiimide hydrochloride (160 mg) was added to a solution of the product of Example 8c (185 mg), 1-hydroxybenzotriazole (110 mg), and the product of Example 1 part o (280 mg) in tetrahydrofuran (3 ml) and the solution stirred at room temperature for 16 hr. The reaction mixture was diluted with ethyl acetate, washed (three times with 1N HCl, brine), dried ($MgSO_4$), and evaporated. The crude product was purified by flash chromatography eluting with acetone:dichloromethane:acetic acid (20:80:1 drop/ml) to afford 160 mg of solid: $R_f$=0.36, methanol:chloroform:acetic acid (5:95:1 drop/ml): HPLC, $t_R$=15.84, Col A, water:acetonitrile:-tetrahydrofuran:trifluoroacetic acid (55:35:15:0.1), FR=2; MS, m/e=684(M+29), 656(M+1), 375, 374, 356, 355, 354, 352, 302, 283, 260, 259, 178, 168.

Analysis for $C_{38}H_{40}ClN_5O_{10}S \cdot 1.0\ H_2O \cdot 1.0\ CH_3CO_2H$:

Calculated: C, 55.07: H, 5.31: N, 8.03.
Found C, 55.05: H, 5.13: N, 8.06.

EXAMPLE 9

(S)-[4-[(4-Chlorophenyl)sulfonylaminocarbonyl]benzoyl]-L-valyl-N-[1-[6-(methoxycarbonyl)benzoxazol-2-yl]carbonyl-2-methylpropyl]-L-prolinamide (Formula I, heterocycle containing X, N and Q=6-(methoxycarbonyl)ol-2-yl, benzoxazol-2-yl, A=CO, L=p-phenylene, $R^4=R^5.S(O_2).NH.CO-$, $R^5=4-ClC_6H_4$)

a.

(1S)-Benzyloxycarbonyl-L-valyl-N-[1-(hydroxy)[6-(methoxycarbonyl)benzoxazol-2-yl]methyl-2-methylpropyl]-L-prolinamide (Formula XIV, heterocycle containing X, N and Q=6-(methoxycarbonyl)benzoxazol-2-yl)

A stirred solution of imidate prepared as described in Example 4b (1.00 g) and 5-carbomethoxy-2-aminophenol (930 mg) in dry ethanol (9 ml) was heated for 4 hr at 60° under nitrogen. The mixture was dissolved in ethyl acetate, washed (twice with 1N NaOH, brine), dried (MgSO$_4$) and evaporated. The crude product was flash chromatographed, eluting with acetone:hexanes (35:65), to afford 300 mg of the product; TLC, $R_f=0.50$, acetone:hexanes (45:55): MS, m/e=610(M+2), 609(M+1).

b.

(S)-Benzyloxycarbonyl-L-valyl-N-[1-[6-(methoxycarbonyl)benzoxazol-2-yl]carbonyl-2-methylpropyl]-L-prolinamide (Formula VI, heterocycle containing X, N and Q=6-(methoxycarbonyl)benzoxazol-2-yl)

t-Butanol (0.050 ml) was added to a solution of the product of Example 9a, (300 mg) and Dess-Martin periodinane (630 mg) in dichloromethane (3 ml) and the solution stirred at room temperature for 17 hr. The resulting suspension was diluted with ethyl acetate and was washed (three portions of 1:1 saturated Na$_2$S$_2$O$_3$:NaHCO$_3$, brine), dried (MgSO$_4$) and evaporated. The crude product was purified by flash chromatography, eluting with acetone:hexane (30:70), to afford a solid which was dissolved in acetonitrile (30 ml) and treated with 300 mg of activated charcoal. The mixture was stirred for 10 min, filtered and evaporated to afford 257 mg of the product; TLC, $R_f=0.49$, acetone:hexanes (40:60): MS, m/e=635(M+29), 608(M+2), 607(M+1).

Analysis for C$_{32}$H$_{38}$N$_4$O$_8$.0.5 H$_2$O:
Calculated: C, 62.43; H, 6.38; N, 9.10.
Found: C, 62.62: H, 6.28: N, 8.94.

c.

(S)-L-Valyl-N-[1-[6-(methoxycarbonyl)benzoxazol-2-yl]carbonyl-2-methylpropyl]-L-prolinamide trifluoromethanesulfonic acid salt (Formula V, heterocycle containing X, N and Q=6-(methoxycarbonyl)benzoxazol-2-yl)

To a stirred solution of the product of Example 9b, (210 mg) in dichloromethane (1.5 ml) under nitrogen was added trifluoromethane sulfonic acid (0.15 ml) dropwise. After 40 min the reaction mixture was evaporated. The resulting solid was placed under vacuum for an hour and used directly in Example 9d, below TLC, $R_f=0.00$ acetone:hexanes (25:75); MS, m/e=244, 242, 235, 195, 189, 186, 181, 178, 121, 105, 93, 92, 91, 79 d.

(S)-[4-[(4-Chlorophenyl)sulfonylaminocarbonyl]benzoyl]-L-valyl-N-[1-[6-(methoxycarbonyl)benzoxazol-2-yl]carbonyl-2-methylpropyl]-L-prolinamide (Formula I, heterocycle containing X, N and Q=6-(methoxycarbonyl)benzoxazol-2-yl, A=CO, L=p-phenylene, $R^4=R^5.S(O_2).NH.CO-$, $R^5=4-ClC_6H_4$)

1-(3-Dimethylaminopropyl)-3-ethylcarbodiimide hydrochloride (75 mg) was added to a solution of the product of Example 9c, above, 1-hydroxybenzotriazole (50 mg) and 4-[(4-chlorophenyl)sulfonylaminocarbonyl]benzoic acid (130 mg) in methylene chloride (2 ml) and tetrahydrofuran (2 ml) followed by the addition of 4-methylmorpholine (0.041 ml) and the solution stirred at room temperature for 16 hr. Additional 4-methylmorpholine (0.041 ml) was added to the reaction mixture and the reaction stirred an additional 7 hr. The reaction mixture was diluted with ethyl acetate, washed (1N HCl (three times), brine), dried (MgSO$_4$), and evaporated. The crude product was purified by flash chromatography, eluting with acetone:methylene chloride:acetic acid (30:70:1), to afford of a solid (160 mg) which was further purified by flash chromatography, using a gradient elution of acetone:methylene chloride:acetic acid (500 ml of 0:100:1; 900 ml of 10:90:1: then 50:50:1), to afford the title compound (71.6 mg); TLC, $R_f=0.17$, acetone:chloroform:acetic acid (10:90:1): HPLC, $t_R=15.84$, Col A, FR=2, water:acetonitrile:tetrahydrofuran:trifluoroacetic acid (55:35:15:0.1): MS, m/e=794(M+1), 778, 777, 776, 423, 422, 421, 384, 374, 357, 356, 355, 354, 259.

Analysis for C$_{38}$H$_{40}$ClN$_5$O$_{10}$S.1.0 H$_2$O.1.5 CH$_3$CO$_2$H:
Calculated: C, 54.57: H, 5.36: N, 7.76.
Found: C, 54.34: H, 5.19: N, 7.81.

EXAMPLE 10

(S)-[4-[(4-Chlorophenyl)sulfonylaminocarbonyl]benzoyl-L-valyl-N-[1-(5-carboxybenzoxazol-2yl)carbonyl-2-methylpropyl]-L-prolinamide (Formula I, heterocycle containing X, N and Q=5-carboxybenzoxazol-2-yl, A=CO, L=p-phenylene, $R^4=R^5.S(O).NH.CO-$, $R^5=4-ClC_6H_4$)

a.

(1S)-Benzyloxycarbonyl-L-valyl-N-[1-(5-carboxybenzoxazol-2-yl)hydroxymethyl-2-methylpropyl]-L-prolinamide (Formula XIV, heterocycle containing X, N and Q=5-carboxybenzoxazol-2-yl)

A stirred solution of imidate prepared as in Example 4b (3.00 g) and 3-amino-4-hydroxybenzoic acid (2.55 g) in dry ethanol (25 ml) was heated for 1.5 hr at 60° under nitrogen, after which time an additional amount of imidate (2.00 g) and amino phenol (1.85 g) were added. The mixture was heated an additional 8.25 hr. The mixture was dissolved in ethyl acetate, washed (1N HCl (twice), brine), dried (MgSO$_4$) and evaporated. The crude product was flash chromatographed, eluting with acetone:hexanes:acetic acid (50:50:1), to afford the product (330 mg); TLC, $R_f=0.19$, acetone:hexanes:acetic acid (50:50:1); MS, m/e=595(M+1), 577.

b.
(1S)-L-Valyl-N-[1-(5-carboxybenzoxazol-2-yl)hydroxymethyl-2-methylpropyl)-L-prolinamide (Formula XV, heterocycle containing X, N and Q=5-carboxybenzoxazol-2-yl)

A mixture of 10% palladium on carbon (1.50 g) and the product of Example 10a (2.90 g) in ethanol (100 ml) was hydrogenated in a shaker at 3.4 bar for 3 hr, after which time the mixture was filtered through diatomaceous earth and the solvent evaporated to afford product (1.95 g): TLC, $R_f$=0.0, methanol:chloroform:acetic acid (5:95:1): MS, m/e=461(M+1), 443, 331, 319, 290, 265, 248, 232, 225, 198, 197, 196, 154.

c.
(1S)-[4-[(4-Chlorophenyl)sulfonylaminocarbonyl]benzoyl]-L-valyl-N-[1-(5-carboxybenzoxazol-2-yl)hydroxymethyl-2-methylpropyl]-L-prolinamide (Formula III, heterocycle containing X, N and Q=5-carboxybenzoxazol-2-yl, A=CO, L=p-phenylene, $R^4$=$R^5$.S($O_2$) NH.CO—, $R^5$=4—$ClC_6H_4$)

Isobutyl chloroformate (0.34 ml) was added dropwise over the course of three min to a stirred, −40° solution of 4-[(4-chlorophenyl)sulfonylaminocarbonyl]benzoic acid (850 mg) and 4-methylmorpholine (0.58 ml) in dry tetrahydrofuran (12 ml). The mixture was stirred for 30 min after which time the product from Example 10b (800 mg) in dimethylformamide (9 ml) was added dropwise to the reaction mixture. The reaction was allowed to warm slowly to room temperature overnight. The resulting mixture was diluted with ethyl acetate, washed (twice with 1N HCl, once with brine), dried (MgSO$_4$), and evaporated. The crude material was flash chromatographed, eluting with acetone:methylene chloride:acetic acid (30:70:1), to afford the product (570 mg): TLC, $R_f$=0.28, acetone: methylene chloride:acetic acid (42:60:1): MS, m/e=782(M+1), 764, 423, 421,377, 193, 191.

d.
(S)-[4-[(4-Chlorophenyl)sulfonylaminocarbonyl]benzoyl-L-valyl-N-[1-(5-carboxybenzoxazol-2-yl)carbonyl-2-methylpropyl]-L-prolinamide (Formula I, heterocycle containing X, N and Q=5-carboxybenzoxazol-2-yl, A=CO, L=p-phenylene, $R^4$=$R^5$.S($O_2$).-NH.CO—, $R^5$=4—$ClC_6H_4$)

t-Butanol (0.070 ml) was added to a solution of the product of Example 10c (560 mg) and Dess-Martin periodinane (910 mg) in dry dichloromethane (3 ml) and the solution stirred at room temperature for 21 hr. The resulting suspension was diluted with ethyl acetate, washed (half saturated Na$_2$S$_2$O$_3$ (three times)), dried (MgSO$_4$), and evaporated. The crude product was purified by flash chromatography, eluting with acetone:dichloromethane:acetic acid (30:70:1), to afford the title compound (100 mg); TLC, $R_f$=0.28, methanol:-chloroform:acetic acid (5:95:1); MS, m/e=781(M+1), 764, 763, 762, 423, 421, 342, 341; HPLC, $t_R$=10.43, Col A, FR=2, water:acetonitrile:tetrahydrofuran:trifluoroacetic acid (55:35:15:0.1).

Analysis for C$_{37}$H$_{38}$ClN$_5$O$_8$S.0.50H$_2$O.1.50 CH$_3$CO$_2$H:
Calculated: C, 54.64: H, 5.16; N, 7.96.
Found: C, 54.64; H, 5.30: N, 7.73.

EXAMPLE 11
[4-(Isopropylsulfonylaminocarbonyl)benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, $R^4$=$R^5$.S($O_2$).NH.CO—, $R^5$=CH(CH$_3$)$_2$)

a. t-Butyl 4-(isopropylsulfonylaminocarbonyl)benzoate 1-(3-Dimethylaminopropyl)-3-ethylcarbodiimide hydrochloride (198 mg) was added to a stirred mixture of 4-(t-butoxycarbonyl)benzoic acid (195 mg), 2-propanesulfonamide (98 mg) and 4-dimethylaminopyridine (126 mg) in dichloromethane (3.7 ml). The mixture was stirred overnight, diluted with ethyl acetate, washed (1N HCl, brine), dried (MgSO$_4$), and evaporated. The crude product was purified by flash chromatography, eluting with acetone:hexanes (75:25), to afford the product (193 mg): TLC, $R_f$=0.64, acetone:hexanes (75:25): MS, m/e=356(M+29), 330(M+3), 329(M+2), 328(M+1), 272, 223, 222, 205, 204, 166.

b. 4-(Isopropylsulfonylaminocarbonyl)benzoic acid

Trifluoroacetic acid (5 ml) was added to the product from Example 11a (193 mg). The resulting solution was stirred 6.5 hr, then evaporated. The crude material product was redissolved in ether and evaporated (four times). The crude product was then added to a volume of hexanes and evaporated (twice) to afford of the product (214 mg): TLC, $R_f$=0.29, acetone:hexanes:acetic acid (50:50:1): MS, m/e=272(M+1), 166, 148, 115, 109, 95.

c.
[4-(Isopropylsulfonylaminocarbonyl)benzoyl]-L-valyl-N-[1-(2-benzoxazolyl)hydroxymethyl-2-methylpropyl]-L-prolinamide (Formula III, heterocycle containing X, N and Q=2-benzoxazolyl, $R^4$=$R^5$.S($O_2$). .NH.CO—, $R^5$=CH(CH$_3$)$_2$).

1-(3-Dimethylaminopropyl)-3-ethylcarbodiimide hydrochloride (166 mg) was added to a stirred solution of the product of Example 1k (362 mg), the product of Example 11b (214 mg) and 1-hydroxybenzotriazole (117 mg) in dichloromethane (3 ml), and the mixture stirred overnight. The reaction mixture was diluted with ethyl acetate, washed (1N HCl (three times)), dried (MgSO$_4$), and evaporated. The crude product was purified by flash chromatography, eluting with tetrahydrofuran:-hexanes:acetic acid (65:35:1) to afford the product (215 mg): TLC, $R_f$=0.44, acetone: hexanes:acetic acid (75:25:1): MS, m/e=671(M+2), 670(M+1), 653, 652, 353, 319, 318, 300, 249, 231, 204, 124, 120.

d.
[4-(Isopropylsulfonylaminocarbonyl)benzoyl]-L-valyl-N-1-(2-benzoxazolyl)carbonyl-2-methylpropyl]-L-prolinamide (Formula I, heterocycle containing X, N and Q=2-benzoxazolyl, L=p-phenylene, $R^4$=$R^5$.S($O_2$).NH.CO—, $R^5$=CH(CH$_3$)$_2$)

Dess-Martin periodinane (408 mg) was added to a stirred solution of the product of Example 11c (215 mg) and t-butanol (0.09 ml) in dichloromethane (3 ml). The resulting suspension was stirred overnight. The reaction mixture was filtered and the solvent evaporated. The resulting oil was filtered through silica gel with acetone:hexanes (65:35) to afford 404 mg of the crude product. This crude product was purified by flash chromatography eluting with tetrahydrofuran:hexanes:acetic acid (55:45:1) and the resulting solid was dissolved in dichloromethane (5 ml) and treated with decolorizing carbon (15 mg). The suspension was filtered and the solvent evaporated to afford the product (130 mg): TLC, $R_f$=0.67, methanol:chloroform:acetic acid (5:95:1); HPLC, $t_R$=9.50, Col B, FR=2, water:acetonitrile:tetrahydrofuran:trifluoroacetic acid (55:35:15:0.1): MS, m/e=696(M+29), 669(M+2), 668(M+1), 651, 650, 353, 317, 316, 309, 299, 298, 297, 296, 201.

Analysis for $C_{33}H_{41}N_5O_8S.0.85\ H_2O$:
Calculated: C, 58.02: H, 6.30; N, 10.25.
Found: C, 58.29: H, 6.17 N, 9.67.

EXAMPLE 12

[4-[(4-Chlorophenyl)sulfonylaminocarbonyl]benzoyl]-L-valyl-N-[1-(2-oxazolyl)carbonyl-2-methylpropyl]-L-prolinamide (Formula I, heterocycle containing X, N and Q=2-oxazolyl, A=CO, L=p-phenylene, $R^4$=$R^5$.S($O_2$).NH.CO—, $R^5$=4—$ClC_6H_4$)

a. 2-Trimethylsilyl oxazole n-Butyllithium (28.5 ml of a 2.54M solution in hexane) was added to a −78° solution of oxazole (5.0 g) in ether (150 ml). The resulting solution was stirred at −78° for 30 min, followed by the addition of trimethylsilyl chloride (7.86 g), and the mixture allowed to warm to room temperature. The reaction mixture was distilled and the fraction with a boiling point of about 130° was collected to afford 2-trimethylsilyl oxazole (5.12 g); MS, m/e=142(M+1), 91, 73.

b.
(1S)-Benzyloxycarbonyl-L-valyl-N-[1-(2-oxazolyl)hydroxymethyl-2-methylpropyl]-L-prolinamide (Formula XIV, heterocycle containing X, N and Q=2-oxazolyl)

A solution of the aldehyde (of formula XI) prepared in a similar manner to that described in Example 1h (7.4 g) and the product of Example 12a (4.84 g) in toluene (10 ml) was heated at 80° for 24 hr and at 60° for an additional 14 hr. The solvents were evaporated, and the residue was dissolved in tetrahydrofuran (50 ml) and treated with 1N HCl (5 ml) and stirred for 30 min. The mixture was dissolved in ethyl acetate, washed (1N HCl, saturated sodium bicarbonate, brine), dried (MgSO4), and evaporated. The crude material was purified by flash chromatography, eluting with acetone:hexanes (30:70), to afford the product (4.57 g): TLC, $R_f$=0.31, methanol:chloroform (5:95): MS, m/e=501(M+1), 483, 393.

Analysis for $C_{26}H_{36}NO_6$:
Calculated: C, 62.38: H, 7.25; N, 11.19.
Found: C, 62.52: H, 7.22; N, 10.87.

c.
(S)-Benzyloxycarbonyl-L-valyl-N-[2-methyl-1-[(2-oxazolyl)carbonyl]propyl]-L-prolinamide (Formula VI, heterocycle containing X, N and Q=2-oxazolyl)

t-Butanol (0.83 ml) was added to a solution of the product of Example 12b (4.4 g) and Dess-Martin periodinane (15 g) in dichloromethane (150 ml) and stirred for 16 hr. The resulting suspension was partitioned between saturated $Na_2S_2O_3$:saturated $NaHCO_3$ (1:1) and ethyl acetate. The ethyl acetate solution was washed (saturated $Na_2S_2O_3$:saturated $NaHCO_3$ (1:1), saturated $NaHCO_3$, brine), dried (MgSO4), and evaporated. The residue was purified by flash chromatography, eluting with acetone:hexanes (35:65), to afford 4.8 g solid. This solid was dissolved in ethyl acetate, washed (saturated Na saturated $NaHCO_3$ (1:1), saturated $NaHCO_3$, brine), dried (MgSO4), and evaporated to afford the product as a white foam (3.74 g); TLC, $R_f$=0.32, acetone:hexanes (40:60): MS, m/e=499 (M+1), 266.

Analysis for $C_{26}H_{34}N_4O_6$:
Calculated: C, 62.64; H, 6.87; N, 11.24.
Found: C, 62.30; H, 6.74; N, 11.01.

d.
[4-[(4-Chlorophenyl)sulfonylaminocarbonyl]benzoyl]-L-valyl-N-[1-(2-oxazolyl)carbonyl-2-methylpropyl]-L-prolinamide (Formula I, heterocycle containing X, N and Q=2-oxazolyl, L=p-phenylene, $R^4$=$R^5$.S($O_2$).NH.CO—, $R^5$=4—$ClC_6H_4$)

Trifluoromethanesulphonic acid (0.89 ml) was added to a solution of the product of Example 12c (1.0 g) in dichloromethane (15 ml) and stirred for 10 min, the solvents evaporated and the residue placed under high vacuum for 20 min. The residue was dissolved in tetrahydrofuran (40 ml) and treated with 1-(3-dimethylaminopropyl)-3-ethylcarbodiimide hydrochloride (429 mg), 4-[(4-chlorophenyl)sulfonylaminocarbonyl]-benzoic acid (800 mg) and 4-dimethylaminopyridine (1.97 g). The mixture was stirred at room temperature for 16 hr, dissolved in ethyl acetate, washed (1N HCl, saturated NaHCO3, brine), dried (MgSO4), and evaporated. The crude material was purified by flash chromatography, eluting with acetone:hexanes:acetic acid (10:90:1 to 20:80:1), to afford the product (930 mg); TLC, $R_f$=0.40, methanol:chloroform:acetic acid (5:95:1); HPLC, $t_R$=7.35, Col A, FR=2, water:acetonitrile:tetrahydrofuran:trifluoroacetic acid (55:35:15:0.1): MS, m/e=686(M+1), 668, 393, 377, 266, 248.

Analysis for $C_{32}H_{36}ClN_5O_8S.0.5\ H_2O.1.0\ CH_3COOH$:
Calcualted: C, 54.07: H, 5.47; N, 9.27.
Found: C, 53.78; H, 5.33: N, 9.25.

EXAMPLE 13

[4-[(4-Chlorophenyl)sulfonylaminocarbonyl]benzoyl]-L-valyl-N-[1-(2-benzothiazolyl)carbonyl-2-methylpropyl]-L-prolinamide (Formula I, heterocycle containing X, N and Q=2-benzothiazolyl, A=CO, L=p-phenylene, $R^4$=$R^5$.S($O_2$).NH.CO—, $R^5$=4—$ClC_6H_4$)

a.
Nα-Benzyloxycarbonyl-N-methoxy-N-methylvalinamide

A solution of 1-(3-dimethylaminopropyl)-3-ethylcarbodiimide hydrochloride (19.07 g) in dichloromethane (500 ml) was cooled to −10°. To this solution were added 1-hydroxybenzotriazole (13.44 g) and 4-methylmorpholine (11.5 ml). A solution of N-(benzyloxycarbonyl)-L-valine (25.0 g) in dichloromethane (200 ml) was added dropwise to the reaction mixture. After addition was complete, the mixture was warmed to ambient temperature and stirred for 0.5 hr before being cooled to 10°. A mixture of N-methyl-O-methylhydroxylamine hydrochloride (9.7 g) and 4-methylmorpholine (11.5 ml) in dichloromethane (150 ml) was added dropwise to the stirred reaction mixture. The reaction was warmed to ambient temperature with overnight stirring. The mixture was evaporated and the residue was partitioned between water and ethyl acetate. The organic layer was washed (10% saturated NaHCO3, brine), dried (MgSO4), evaporated and dried overnight under high vacuum to give the product as a gum (26.25 g) which solidified in the freezer; TLC: $R_f$=0.57, chloroform:methanol (40:1); MS, m/e=295(M+1), 234, 187, 162, 152, 119.

b. (S)-1-(2-Benzothiazolyl)-2-(benzyloxycarbonyl)amino-3-methyl-1-butanone

Dry ether (5 ml) was cooled to −78° and n-butyllithium (6.0 ml of 2.54M solution in hexanes) was added. A dry ether (15 ml) solution of benzothiazole (1.83 g) was added rapidly dropwise. Stirring at −78° was continued for 10 min. An ether (10 ml) solution of amide prepared according to the procedure of Example 13a and used without further purification (2.00 g) was added via cannula, and the reaction mixture was allowed to warm to 30° with stirring for 1 hr. The reaction mixture was quenched by pouring into saturated NH₄Cl and extracted with ethyl acetate. The extracts were dried (Na₂SO₄) and evaporated to give a yellow oil. Purification by flash chromatography, eluting with hexane:ethyl acetate (10:1), gave the product as a yellow glass (0.98 g): TLC, $R_f$=0.67, hexane:ethyl acetate (2:1); MS, m/e=368(M+1), 206, 191, 162, 135, 91 (base).

c. 2-Amino-1-(2-benzothiazolyl)-3-methyl-1-butanone

Material prepared according to the procedure of Example 13b (0.94 g) was dissolved in a mixture of dichloromethane (20 ml) and anisole (1 ml) under nitrogen. Trifluoromethanesulfonic acid (1 ml) was added and the reaction was stirred for 10 min. The reaction was diluted with dichloromethane and extracted with water. The aqueous extracts were washed with dichloromethane, brought to pH=8 with saturated NaHCO₃ and extracted with dichloromethane. The organic solution was dried (Na₂SO₄) and evaporated to give a yellow oil (0.50 g); TLC, $R_f$=0.36, hexane:ethyl acetate (2:1).

d. Benzyloxycarbonyl-L-valyl-N-[1-(2-benzothiazolyl)carbonyl-2-methylpropyl]-L-prolinamide (Formula VI, heterocycle containing X, N and Q=2-benzothiazolyl)

A dichloromethane solution of material prepared according to the procedure of Example 13c and used without further purification (0.5 g), 1-hydroxybenzotriazole (0.58 g) and product prepared according to the method of Example 1f (0.74 g) was treated with 1-(3-dimethylaminopropyl)-3-ethylcarbodiimide hydrochloride (0.47 g), and the reaction mixture was stirred under nitrogen for 15 hr. The reaction mixture was diluted with dichloromethane, washed (saturated NaHCO₃, 10% HCl), dried (Na₂SO₄) and evaporated to give a yellow oil (1.48 g): TLC, $R_f$=0.39, chloroform:methanol (50:1); MS, m/e=565(M+1, base), 332, 331.

e. L-Valyl-N-[1-(2-benzothiazolyl)carbonyl-2-methylpropyl]-L-prolinamide (Formula V, heterocycle containing X, N and Q=2-benzothiazolyl)

Amide prepared according to the procedure of Example 13d and used without further purification (1.20 g) was deprotected using a similar procedure to the procedure of Example 13c to give the product as an oil (0.34 g, 37%); TLC: $R_f$=0.34, chloroform:methanol (10:1).

f. [4-[(4-Chlorophenyl)sulfonylaminocarbonyl]benzoyl]-L-valyl-N-[1-(2-benzothiazolyl)carbonyl-2-methylpropyl]-L-prolinamide (Formula I, heterocycle containing X, N and Q=2-benzothiazolyl, A=CO, L=p-phenylene, $R^4$=$R^5$.S(O).NH.CO—, $R^5$=4—ClC₆H₄)

Amine prepared according to the procedure of Example 13e and used without further purification (0.34 g), 1-hydroxybenzotriazole (0.21 g) and 4-[(4-chlorophenyl)sulfonylaminocarbonyl]benzoic acid (0.27 g) were combined in dichloromethane (12 ml) and the suspension was treated with 1-(3-dimethylaminopropyl)-3-ethylcarbodiimide hydrochloride (0.17 g). Stirring was continued for 7.5 hr. The reaction was diluted with ethyl acetate and washed (saturated NaHCO₃, 10% HCl), dried (Na₂SO₄) and evaporated to give an oily foam. Purification by flash chromatography, eluting with hexanes:ethyl acetate:acetic acid (50:50:1.5), gave the product as a white solid (0.32 g): TLC, $R_f$=0.29, hexanes:ethyl acetate:acetic acid (50:50:1.5); HPLC, $t_R$=26, Col A, FR=2, water:acetonitrile:tetrahydrofuran:trifluoro acetic acid (55:35:15:0.1); MS, m/e=752(M+1), 423, 421, 393, 377, 342, 332, 315, 314 (base), 313, 312, 136.

Analysis for C₃₆H₃₈ClN₅O₇S₂.0.3 CH₃COOH:
Calculated: C, 57.07; H, 5.13; N, 9.09.
Found: C, 57.32: H, 5.45: N, 8.76.

EXAMPLE 14

(S)-[4-[(4-Chlorophenyl)sulfonylaminocarbonyl]benzoyl]-L-valyl-N-[2-methyl-1-(2-thiazolyl)carbonylpropyl]-L-prolinamide (Formula I, heterocycle containing X, N and Q=2-thiazolyl, A=CO, L=p-phenylene, $R^4$=$R^5$.S(O₂).NH.CO—, $R^5$=4—ClC₆H₄)

a. (S)-2-(Benzyloxycarbonyl)amino-3-methyl-1-(2-thiazolyl)-1-butanone

To a cooled (−35°) solution of thiazole (1.23 ml) in dry tetrahydrofuran (40 ml) was added n-butyllithium (6.6 ml of a 2.18M solution in hexane) over 3 min. The dark brown reaction mixture was stirred in the temperature range −30° to −25° for 10 min. A solution of material prepared according to the procedure of Example 13a and used without further purification (1.7 g) in dry tetrahydrofuran (15 ml) was added rapidly over 1 min. Stirring at −30° was continued for 15 min. The mixture was quenched by pouring it into saturated NH₄Cl (100 ml), and the organics were extracted into ethyl acetate. The extracts were washed (saturated NaHCO₃), dried (Na₂SO₄) and evaporated to give a brown oil. Purification by flash column chromatography, eluting with hexane:ethyl acetate (2:1), gave the product as a yellow oil (1.81 g, 98%); TLC, $R_f$=0.45, hexane:ethyl acetate (2:1): MS, m/e=319(M+1, base), 275.

b. (S)-2-Amino-3-methyl-1-(2-thiazolyl)-1-butanone

Ketone prepared according to the procedure of Example 14a (1.8 g) was dissolved in dichloromethane (30 ml) and treated with trifluoromethanesulfonic acid (2.5 ml) in a single portion, and the reaction was stirred at ambient temperature for 5 min. The mixture was diluted with dichloromethane and extracted with water. The aqueous phase was brought to basic pH with saturated NaHCO$_3$ and then was extracted with dichloromethane. The extracts were dried (Na$_2$SO$_4$) and evaporated to give the product as a dark yellow oil (0.78 g, 75%): TLC, R$_f$=0.7, chloroform:methanol (10:1): MS, m/e=185(M+1, base), 167, 140.

c.
(S)-Benzyloxycarbonyl-L-valyl-N-[2-methyl-1-(2-thiazolyl)carbonylpropyl]-L-prolinamide (Formula VI, heterocycle containing X, N and Q=2-thiazolyl)

Amino ketone prepared according to the procedure of Example 14b (0.73 g) was dissolved in dichloromethane (25 ml). Sequentially added to the solution were benzyloxycarbonyl-L-valyl-L-proline (1.38 g), 1-hydroxybenzotriazole (1.07 g) and 1-(3-dimethylaminopropyl)-3-ethylcarbodiimide hydrochloride (0.76 g). The mixture was stirred overnight at ambient temperature under nitrogen. The reaction mixture was diluted with dichloromethane, washed (saturated NaHCO$_3$, 10% HCl), dried (Na$_2$SO$_4$) and evaporated to give a yellow oil (2.5 g). Purification by flash chromatography, eluting with hexane:ethyl acetate (1:1) gave the product as a solid foam (1.61 g): TLC, R$_f$=0.3, hexane:ethyl acetate (1:1): MS, m/e=515(M+1, base), 407, 331, 282, 91.

Analysis for C$_{26}$H$_{34}$N$_4$O$_5$S.0.5 H$_2$O:
Calculated: C, 59.64; H, 6.74: N, 10.70.
Found: C, 59.56: H, 6.54: N, 10.42.

d.
(S)-L-Valyl-N-[2-methyl-1-(2-thiazolyl)carbonylpropyl]-L-prolinamide trifluoromethanesulfonic acid salt (Formula V, heterocycle containing X, N and Q=2-thiazolyl)

Ketone prepared according to Example 14c (0.51 g) was dissolved in dichloromethane (15 ml) and was treated with trifluoromethanesulfonic acid (0.44 ml) in a single portion. The reaction mixture was stirred at ambient temperature for 15 min. Evaporation and drying under high vacuum gave a white gum (1.17 g, more than 100%). The weight of crude product in excess to 100% yield was assumed to be trifluoromethanesulfonic acid.

e.
(S)-[4[(4-Chlorophenyl)sulfonylaminocarbonyl]benzoyl]-L-valyl-N-[2-methyl-1-(2-thiazolyl)carbonylpropyl]-L-prolinamide (Formula I, heterocycle containing X, N and Q=2-thiazolyl, A=CO, L=p-phenylene, R$^4$=R$^5$.(SO$_2$).NH.CO—, R$^5$=4—ClC$_6$H$_4$)

Crude amino ketone prepared according to the procedure of Example 14d and used without further purification (1.14 g), 1-hydroxybenzotriazole (0.13 g), 4-[(4-chlorophenyl)sulfonylaminocarbonyl]benzoic acid (0.34 g) and 4-methylmorpholine (0.59 ml) were dissolved in tetrahydrofuran and the mixture was treated with 1-(3-dimethylaminopropyl)-3-ethylcarbodiimide hydrochloride. The mixture was stirred overnight under nitrogen. Evaporation gave a residue which was partitioned between water and ethyl acetate. The organic phase was washed (10% HCl, water, brine), dried (MgSO$_4$) and evaporated. Flash chromatography, eluting with chloroform:methanol:acetic acid (100:2.5:0.5), gave the product as a white foam (0.50 g). A second purification (same solvent system as above) yielded the title product as a white foam (0.43 g); TLC, R$_f$=0.35, chloroform:methanol:acetic acid (100:2.5:0.5): MS, m/e=702 ($^{35}$Cl-M+1), 283, 282 (base), 120; HPLC, t$_r$=8.54, Col A, FR=2, water:acetonitrile:tetrahydrofuran:trifluoroacetic acid (55:35:15:0.1).

EXAMPLE 15
(S)-[4-[N'-(Phenylsulfonyl)ureido]benzoyl]-L-valyl-N-[1-(2-benzoxazoyl)carbonyl-2-methylpropyl]-L-prolinamide (Formula I, heterocycle containing X, N and Q=2-benzoxazoyl, A=CO, L=p-phenylene, R$^4$=R$^5$.S(O$_2$).NH.CO.NR$^6$—, R$^5$=C$_6$H$_5$, R$^6$=H)

a. 4-[N'-(Phenylsulfonyl)ureido]benzoic acid

To a stirred solution of p-aminobenzoic acid (3.48 g) and 4-methylmorpholine (2.75 ml) in distilled tetrahydrofuran (110 ml) was added phenylsulfonyl isocyanate (4.65 g). The reaction mixture, which warmed slightly upon addition, was stirred for 18 hr, diluted with 1N HCl, and extracted with methylene chloride. The organic extracts were washed (1N HCl (twice), brine), dried (Na$_2$SO$_4$), filtered and evaporated to afford a yellowish solid. This solid was triturated with ether and filtered to afford the product as a white solid (5.26 g, 65%); TLC, R$_f$=0.25, methanol:chloroform:acetic acid (5:95:1): MS, 321(M+1), 303, 277, 257, 184, 164, 160, 159, 158, 141, 140, 139, 138, 137, 120, 94.

b.
(1S)-Benzyloxycarbonyl-L-valyl-N-[1-(2-benzoxazoyl)-hydroxymethyl-2-methylpropyl]-L-prolinamide (Formula XIV, heterocycle containing X, N and Q=2-benzoxazoyl)

To a stirred solution of ethanol (42.3 ml) in chloroform (44 ml) at 0° was added dropwise acetyl chloride (46.5 ml) over 25 min. The mixture was stirred an additional 10 min. Cyanohydrin prepared as described in Example 4a (10.0 g), was added to the mixture, followed by an additional volume of chloroform (44 ml). The reaction mixture was stirred at 0° for 3 hr and the solvents evaporated to afford a white foam which was dissolved in ethanol (100 ml). To this ethanolic solution was added 2-aminophenol (7.14 g), and the resulting brown mixture was heated to 60° with stirring under nitrogen for 45 min. The reaction mixture was cooled, diluted with ether, washed (1N NaOH (5 times), brine), dried (Na$_2$SO$_4$K$_2$CO$_3$(2:1 v/v)), and evaporated to obtain a brown foam (10.3 g). The crude material was purified by flash chromatography, eluting with acetone:hexanes (35:65), to afford the product (4.92 g): TLC, R$_f$=0.24, methanol: chloroform (5:95): MS, m/e=551(M+1), 331, 148, 108, 91.

Analysis for C$_{30}$H$_{38}$N$_4$O$_6$0.50 H$_2$O:
Calculated: C, 64.39: H, 7.02; N, 10.01.
Found: C, 64.29; H, 6.87: N, 9.86.

c.
(1S)-L-Valyl-N-[1-(2-benzoxazolyl)hydroxymethyl-2-methylpropyl]-L-prolinamide (Formula XV, heterocycle containing X, N and Q=2-benzoxazolyl).

A mixture of 10% (w/w) palladium on carbon (800 mg, 50% (w/w) water wet) and the product from Example 15b (4.90 g) in ethanol (250 ml) was hydrogenated in a shaker at 3.4 bar for 2 hr, after which time an additional portion of catalyst (0.500 g) was added. The mixture was hydrogenated in a shaker at 3.4 bar for an additional 2 hr, filtered through diatomaceous earth and evaporated to afford the product as a solid (3.67 g, 99%), TLC, R$_f$=0.42, methanol:chloroform (5:95); MS, m/e=445(M+29), 418(M+2), 417(M+1).

d.
(1S)-[4-[N'-(Phenylsulfonyl)ureido]benzoyl]-L-valyl-N-[1-(2-benzoxazolyl)hydroxymethyl-2-methylpropyl]-L-prolinamide (Formula III, heterocycle containing X, N, and Q=2-benzoxazolyl, A=CO, L=p-phenylene, R$^4$=R$^5$.S(O).NH.CO.NR$^6$—, R$^5$=C$_6$H$_5$, R$^6$=H)

1-(3-Dimethylaminopropyl)-3-ethylcarbodiimide hydrochloride (190 mg) was added to a solution of the product of Example 15c (380 mg), 1-hydroxybenzotriazole (140 mg), and 4-[N'-(phenylsulfonyl)ureido]benzoic acid (320 mg) in dimethylformamide (5 ml) and the solution stirred at room temperature for 16 hr. The reaction mixture was diluted with ethyl acetate, washed (1N HCl (three times), brine), dried (MgSO$_4$), and evaporated. The crude product was flash chromatographed, eluting with ethyl acetate:chloroform:acetic acid (50:50:1) to afford the product as a solid (460 mg); TLC, R$_f$=0.14, methanol:chloroform:acetic acid (5:95:1).

Analysis for C$_{36}$H$_{44}$N$_6$O$_8$S.1.0 H$_2$O.1.0 CH$_3$CO$_2$H:
Calculated: C, 57.13: H, 6.31: N, 10.51.
Found: C, 58.39; H, 6.33: N, 9.95.

e.
(S)-[4-[N'-(Phenylsulfonyl)ureido]benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, R$^4$=R$^5$.S(O$_2$).NH.CO.NR$^6$—, R$^5$=C$_6$H$_5$, R$^6$=H)

Dess-Martin periodinane (440 mg) was added to a solution of t-butanol (0.048 ml) and the product of Example 15d, (370 mg) in dry methylene chloride (2.5 ml). The mixture immediately darkened and was allowed to stir for 22 hr. The resulting suspension was diluted with methylene chloride, washed (1:1 (v/v) saturated sodium thiosulfate/sodium bicarbonate (3 times), brine), dried (MgSO$_4$), and evaporated to afford 450 mg of crude oil. This was flash chromatographed, eluting with ethyl acetate:dichloromethane: acetic acid (50:50:1), then rechromatographed using the same system to afford the title compound (91 mg); TLC, R$_f$=0.22, ethyl acetate:dichloromethane:acetic acid (50:50:1); HPLC, t$_R$8.46, Col B, FR=2, water: acetonitrile:tetrahydrofuran:trifluoroacetic acid (55:35:15:0.1): MS, m/e=640, 317, 316, 298, 245, 219, 197, 120.

Analysis for C$_{36}$H$_{40}$N$_6$O$_8$S.1.0 H$_2$O.2.0 CH$_3$CO$_2$H:
Calculated: C, 56.20: H, 5.89; N, 9.83.
Found C, 56.08; H, 5.93; N, 9.33.

EXAMPLE 16

(S)-[4-[N'-[(4-Chlorophenyl)sulfonyl]ureido]benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, R$^4$=R$^5$.S(O$_2$).NH.CO.NR$^6$—, R$^5$=4—ClC$_6$H$_4$, R$^6$=H)

a. 4-[N'-[(4-Chlorophenyl)sulfonyl]ureido]benzoic acid

To a stirred solution of p-aminobenzoic acid (2.68 g) and 4-methylmorpholine (2.15 ml) in distilled tetrahydrofuran (90 ml) was added chlorophenylsulfonyl isocyanate (4.25 g). The reaction mixture, which warmed slightly upon addition, was stirred for 18 hr. The reaction mixture was acidified with 1N HCl, and a flocculent precipitate formed. The mixture was extracted with methylene chloride, leaving much of the precipitate. Evaporating the methylene chloride solution and triturating the resulting solid with ether afforded 1.25 g of a white solid. The original solid precipitate was lixiviated with methanol, and the resulting solution was evaporated to afford a white solid which was triturated with ether to afford an additional 4.90 g (total yield 5.15 g, 89%) of white solid; TLC, R$_f$=0.21, methanol:chloroform:acetic acid (5:95:1); MS, m/e=355(M+1), 220, 219, 218, 192, 177, 175, 164, 139, 138, 120, 94.

b.
(1S)-[4-[N'-[(4-Chlorophenyl)sulfonyl]ureido]benzoyl]-L-valyl-N-[1-(2-benzoxazolyl)hydroxymethyl-2-methylpropyl]-L-prolinamide (Formula III, heterocycle containing X, N and Q=2-benzoxazolyl, A=CO, L=p-phenylene, R$^4$=R$^5$.S(O$_2$).NH.CO.NR$^6$—, R$^5$=4—ClC$_6$H$_4$, R$^6$=H)

1-(3-Dimethylaminopropyl)3-ethylcarbodiimide hydrochloride (210 mg) was added to a solution of the product of Example 15c (360 mg), 4-dimethylaminopyridine (130 mg), and 4-[N'-[(4-chlorophenyl)sulfonyl]ureido]benzoic acid (507 mg) in tetrahydrofuran (5 ml): and the solution stirred at room temperature for 16 hr. The reaction mixture was diluted with ethyl acetate, washed (distilled water (3 times), 1N HCl, saturated sodium bicarbonate, brine). The bicarbonate wash was acidified to pH=1 and washed three times with ethyl acetate. The combined organic phases were washed (brine), dried (Na$_2$SO$_4$), and evaporated. The crude product was flashed chromatographed, eluting with tetrahydrofuran:chloroform:acetic acid (70:30:1). The resulting material was filtered through silica gel using tetrahydrofuran: chloroform:acetic acid (30:70:1 to 100:0:1) to afford the product (350 mg) as a solid: TLC, R$_f$=0.55, tetrahydrofuran:chloroform:acetic acid (80:20:1); MS, m/e=247, 197, 163.

Analysis for C$_{37}$H$_{41}$ClN$_6$O$_9$S.4.0 H$_2$O.5.0 CH$_3$CO$_2$H:
Calculated: C, 48.94: H, 6.03; N, 7.29.
Found: C, 48.64: H, 5.16: N, 7.53.

c.
(S)-[4-[N'-[(4-Chlorophenyl)sulfonyl]ureido]benzoyl]-L-valyl-N-[1-(2-benzoxazolyl)carbonyl-2-methylpropyl]-L-prolinamide (Formula I, heterocycle containing X, N and Q=2-benzoxazolyl, A=CO, L=p-phenylene, R$^4$=R$^5$.S(O$_2$).NH.CO.NR$^6$—, R$^5$=4—ClC$_6$H$_4$, R$^6$=H)

Dess-Martin periodinane (500 mg), was added to a solution of t-butanol (0.055 ml) and the product from Example 16b (440 mg) in dry methylene chloride (3 ml). The mixture immediately darkened and was allowed to stir for 22 hr. The resulting suspension was diluted with ethyl acetate, washed (1:1 (v/v) saturated sodium thiosulfate:sodium bicarbonate (3 times)), dried (MgSO$_4$). and evaporated to afford 570 mg of an oil. This was flash chromatographed, eluting with acetone:methylene chloride:acetic acid (60:40:1), to afford the title compound (95 mg): TLC, R$_f$=0.50, methanol:chloroform:acetic acid (10:90:1): HPLC, t$_R$=14.68, Col B, FR=2, water:acetonitrile: tetrahydrofuran:trifluoroacetic acid (55:35:15:0.1): MS, m/e=317, 316, 219, 192, 120.

Analysis for C$_{36}$H$_{39}$ClN$_6$O$_8$S.1.0 CH$_3$CO$_2$H:
Calculated: C, 56.26: H, 5.34; N, 10.36.
Found: C, 56.23: H, 5.50; N, 10.59.

EXAMPLE 17

(S)-[4-[N'-[(4-Chlorophenyl)sulfonyl]ureido]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4=R^5.S(O_2).NH.CO.NR$, $R^5=4-Cl_6H_4$, $R^6=H$)

a.

(S)-L-Valyl-N-[1-[5-(methoxycarbonyl)benzoxazol-2-yl]carbonyl-2-methylpropyl]-L-prolinamide (Formula V, heterocycle containing X, N, and Q=5-(methoxycarbonyl)benzoxazol-2-yl)

To a stirred solution of the product of Example 8b (1.00 mg) in methylene chloride (8 ml) under nitrogen was added dropwise trifluoromethanesulfonic acid (0.73 ml). After 10 min the reaction mixture was diluted with dichloromethane and washed three times with distilled water. The pH of the resulting solution was adjusted to pH 8 by the addition of a solution of saturated sodium bicarbonate (25 ml). The basic solution was vigorously extracted with dichloromethane six times. Sodium chloride (10 g) was added to the remaining aqueous layer, and it was extracted twice with dichloromethane. All the organic extracts were combined, dried ($Na_2SO_4$) and evaporated to afford the product (620 mg); TLC, $R_f=0.20$, methanol:chloroform, (5:95).

b.

(S)-[4-[N'-[(4-Chlorophenyl)sulfonyl]ureido]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4=R^5.S(O_2).NH.CO.NR^6$, $R^5=4-ClC_6H_4$, $R^6=H$)

1-(3-Dimethylaminopropyl)3-ethylcarbodiimide hydrochloride (100 mg), was added to a solution of the product of Example 17a (225 mg), 1-hydroxybenzotriazole (70 mg), and 4-[N'-[(4-chlorophenyl)sulfonyl]ureido]benzoic acid (190 mg) in dichloromethane (3 ml) and the solution stirred at room temperature for 16 hr. The reaction mixture was diluted with ethyl acetate, washed (1N HCl (3 times), brine), dried ($MgSO_4$), and evaporated. The crude product was purified by flash chromatography, eluting with acetone:methylene chloride:acetic acid (10:90:1), to afford the title compound (271 mg) as a solid: TLC, $R_f=0.14$, acetone:dichloromethane:acetic acid (20:80:1); HPLC, $t_R=13.47$, Col A, FR=2, water:acetonitrile:tetrahydrofuran:trifluoroacetic acid (55:35:15:0.1); MS, m/e=699, 374, 245, 219, 197, 178, 120.

Analysis for $C_{38}H_{44}ClN_6O_{10}S.3.7$ $H_2O.0.70$ $CH_3CO_2H$:

Calculated: C, 51.55; H, 5.62 N, 9.15.
Found: C, 51.40: H, 4.97: N, 9.48.

EXAMPLE 18

[4-[(Trifluoromethylsulfonyl)amino]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4=CF_3.S(O_2).NH—$)

a. Ethyl 4-[(trifluoromethylsulfonyl)amino]benzoate

Trifluoromethanesulfonic anhydride (4.1 ml) was added dropwise to a precooled (0°) solution of ethyl p-aminobenzoate (3.3 g) in dichloromethane (50 ml) under nitrogen. The reaction mixture was stirred for 1 hr at 0°, then was allowed to warm to room temperature and was stirred for 1 hr. After the reaction mixture was evaporated, ethyl acetate (125 ml) was added to the residue: and the resultant organic solution was washed (1N HCl, then brine), dried ($MgSO_4$), and evaporated. The residue was purified by flash chromatography, eluting with chloroform:methanol (95:5), to give the product as a white powder (1.27 g): TLC, $R_f=0.37$, chloroform:methanol (90:10).

b. 4-[(Trifluoromethylsulfonyl)amino]benzoic acid

A solution of 1N NaOH (8.4 ml) was added to a stirred solution of the product of Example 18a (1.25 g) in methanol (25 ml). Water (2 ml) was added, and the reaction mixture was stirred overnight. After the methanol was distilled off under water aspiration vacuum, the resulting aqueous residue was diluted with water (20 ml). The aqueous solution was washed with ethyl acetate, made acidic (pH 2) with 1N HCl, and extracted with ethyl acetate (total=40 ml). The organic phase was dried ($MgSO_4$) and evaporated to give the product as a white powder (1.05 g): TLC, $R_f=0.4$, chloroform:methanol:acetic acid (96:4:0.2).

c.

(S)-L-Valyl-N-[1-[5-(methoxycarbonyl)benzoxazol-2-yl]carbonyl-2-methylpropyl]-L-prolinamide (Formula V, heterocycle containing X, N, and Q=5-(methoxycarbonyl)benzoxazol-2-yl)

To a stirred solution of the product of Example 8b (750 mg) in methylene chloride (5 ml) under nitrogen was added dropwise trifluoromethanesulfonic acid (0.53 ml). After 20 min the reaction mixture was diluted with dichloromethane and washed three times with distilled water. Sodium chloride (5 g) was added to the combined aqueous layers and the resulting solution was adjusted to pH 8 by the addition of a solution of saturated sodium bicarbonate (20 ml). The basic solution was vigorously extracted with dichloromethane eight times. The organic layers were combined, dried ($Na_2SO_4$) and evaporated to afford the product (420 mg): TLC, $R_f=0.28$, methanol:chloroform (5:95).

d.

[4-[(Trifluoromethylsulfonyl)amino]benzoyl]-L-valyl-N-[1-[5-(methoxycarbonyl)benzoxazol-2-yl]carbonyl-2-methylpropyl]-L-prolinamide (Formula I, heterocycle containing X, N and Q=5-(methoxycarbonyl)benzoxazol-2-yl, A=CO, L=p-phenylene, $R^4=CF_3.S(O_2).NH—$)

1-(3-Dimethylaminopropyl)-3-ethylcarbodiimide hydrochloride (240 mg) was added to a solution of the product of Example 18c (420 mg), 4-dimethylaminopyridine (110 mg), and 4-[(trifluoromethylsulfonyl)amino]benzoic acid (340 mg) in tetrahydrofuran (3 ml); and the solution stirred at room temperature for 16 hr. The reaction mixture was diluted with ethyl acetate, washed (1N HCl (3 times), brine), dried (MgSO$_4$), and evaporated. The crude product was purified by flash chromatography, eluting with methanol:-chloroform:acetic acid (20:80:1), to afford the title compound (330 mg) as a solid: TLC R$_f$=0.50, methanol:-chloroform:acetic acid (5:95:1); HPLC, t$_R$=15.61, Col A, water:acetonitrile:tetrahydrofuran:acetic acid (55:35:15:0.1), FR=2; MS, m/e=752(M+29), 724(M+1), 706, 374, 356, 351, 323.

Analysis for C$_{32}$H$_{36}$F$_3$N$_5$O$_9$S.0.60 H$_2$O.0.80 CH$_3$CO$_2$H:

Calculated: C, 51.57: H, 5.20: N, 8.95.
Found: C, 51.29: H, 5.07; N, 8.97.

EXAMPLE 19

S-[4-[(4-Chlorophenyl)sulfonylaminocarbonyl]benzoyl]-L-valyl-N-[1-[5-(aminocarbonyl)benzoxazol-2-yl]carbonyl-2-methylpropyl]-L-prolinamide (Formula I, heterocycle containing X, N and Q=5-(aminocarbonyl)benzoxazol-2-yl, A=CO, L=p-phenylene, R$^4$=R$^5$.S(O$_2$).NH.CO—, R$^5$=4—ClC$_6$H$_4$)

Method A

Material prepared as described in Example 6 and estimated to contain at least 95% of the (S)-diastereomer (200 mg) was dissolved in hot chloroform (15 ml), filtered, and diluted to a total volumn of 25 ml with hot chloroform. Toluene (5 ml) was added until the solution just turned cloudy and a few drops of chloroform were added resulting in a clear solution. The solution was allowed to cool slowly. After 4 days, the supernatent was removed by filtration and the crystallized solid was dried under nitrogen to afford 101 mg white solid mp 165°-180°: [α]$_D^{25}$=−73.2° (c=2.5, CH$_3$OH).

Method B a. Benzyloxycarbonyl-L-valyl-L-proline t-butyl ester

N-Benzyloxycarbonyl-L-valine (121.3 g), 1-hydroxybenzotriazole (130.5 g) and dry dimethylformamide (DMF) (800 ml) were placed in a 5 liter, 3-necked flask equipped with a mechanical stirrer, thermometer, and a calcium sulfate drying tube, under nitrogen atmosphere. The mixture was cooled to 0° for 15 min and proline t-butyl ester (82.6 g) in dry DMF (800 ml) was added at a fast dropwise rate over 2 h while the temperature of the reaction mixture was maintained at 0°. Dicyclohexylcarbodiimide (109.4 g) in dry DMF (400 ml) then was added in one portion to the reaction mixture. The reaction was stirred at 0° for 3 h, allowed to warm to room temperature gradually over 1 h, and stirred for 48 h, whereupon the reaction was shown to be complete by TLC [R$_f$=0.55, chloroform:ethyl acetate (85:15)]. The reaction mixture was chilled in ice/water and filtered cold to remove the precipitated dicyclohexyl urea. The DMF was evaporated using a mechanical vacuum pump and at a maximum bath temperature of 40°. The remaining oil was diluted with ethyl acetate (2 liter), chilled, and refiltered to remove additional dicyclohexyl urea. The ethyl acetate solution was washed (20% (w/v) citric acid solution (twice), saturated sodium chloride solution, saturated sodium bicarbonate solution (twice), and saturated sodium chloride solution), dried (MgSO$_4$), and evaporated to afford crude benzyloxycarbonyl-L-valyl-L-proline t-butyl ester as an amber oil (208.3 g, 100%).

b. L-Valyl-proline t-butyl ester

A solution of benzyloxycarbonyl-L-valyl-L-proline t-butyl ester (51.8 g) dissolved in absolute ethanol (1 liter) was placed in a 2 liter hydrogenation bottle. The reaction mixture was purged with nitrogen, and 10% (w/w) palladium on carbon catalyst (10 g, 50% (w/w) water wet) was added. The reaction was placed on a large shaker apparatus and shaken at room temperature under a hydrogen atmosphere (3.4 bar). After 1 h, hydrogen uptake ceased. The reaction mixture was checked by TLC [chloroform:ethyl acetate (85:15)] and shown to contain considerable starting material (R$_f$=0.55). Fresh catalyst (10 g) was added, and the reaction was placed back on the apparatus for another 4 h, at which point hydrogen uptake ceased. TLC of the reaction mixture showed complete absence of starting material. The reaction mixture was filtered through a pad of diatomaceous earth, and the filter cake was washed with ethanol. Evaporation of the ethanol from the condensed solution left a cloudy yellow oil. This oil was dissolved in ether (1 liter), filtered to remove a small amount of precipitate (dicyclohexylurea) and evaporated to give crude L-valyl-L-proline t-butyl ester as a yellow oil (32.1 g, 93%).

c. [4-[(4-Chlorophenyl)sulfonylaminocarbonyl]benzoyl]-L-valyl-L-proline t-butyl ester 4-Dimethylaminopyridine (16.4 g) was added to a solution of 4-[(4-chlorophenyl)sulfonylaminocarbonyl]-benzoic acid (45.6 g) in methylene chloride (250 ml). The mixture was stirred 15 min before amine from Example 19b (39.9 g) in dichloromethane (250 ml) and 1-(3-dimethylaminopropyl)-3-ethylcarbodiimide (28.3 g), successively, were added. The reaction mixture was stirred 16 h and additional amine (1.1 g) and carbodiimide (1.5 g) were added to the reaction mixture. After an additional 3 h, the reaction was evaporated to afford a thick, grey syrup. This was dissolved in ethyl acetate, washed (20% w/w citric acid (3 times), brine (4 times)), dried (MgSO$_4$), and evaporated. The crude material was flash chromatographed, eluting with methanol:-methylene chloride (gradient: 0:1 (1.5 liter), 2:98 (1.5 liter), 4:96 (1.5 liter), 5:95 (4 liter)), to afford [4-[(4-chlorophenyl)sulfonylaminocarbonyl]benzoyl]-L-valyl-L-proline t-butyl ester (65.5 g, 73%) as a white foam; TLC, R$_f$=0.50, methanol:dichloromethane:acetic acid (2:98:1).

d. [4-[(4-Chlorophenyl)sulfonylaminocarbonyl]benzoyl]-L-valyl-L-proline (Formula IXa, A=CO, L=p-phenylene, R$^4$=R$^5$.S(O$_2$).NH.CO—, R$^5$=4—ClC$_6$H$_4$)

The product from Example 19c (65.5 g) was dissolved in trifluoroacetic acid (200 ml) with stirring under a nitrogen atmosphere at 0°. After one hour the reaction mixture was cooled to −15° for 16 h, after which time the reaction was poured into ice water (2 liter) with vigorous stirring. The precipitate was filtered, washed with three portions of cold water and dried under reduced pressure. The crude product was redissolved in trifluoroacetic acid (200 ml) and stirred at room temperature 18 h. The reaction mixture was poured into of ice water (1.5 liter) with vigorous stirring. The precipitate was filtered and dried under high vacuum to afford the acid (59.7 g): TLC, $R_f=0.05$; methanol:chloroform:acetic acid (5:95:1). For further purification, the above acid (59.7 g) and calcium oxide (6.25 g) were dissolved in water (500 ml) and tetrahydrofuran (500 ml), and heated at 55°-60° for 0.5 h. After cooling to room temperature, the mixture was concentrated under reduced pressure. The aqueous phase was decanted from the gummy residue and lyophilized to afford a yellow-white powder (47.3 g). This material was crystallized from methanol:water and converted back into the free acid by dissolving it in water and treating the solution with 1N HCl (pH 2) and filtering the precipitated solid.

e. N-Benzyloxycarbonyl-L-valinal

To a solution of the product of Example 1c (27.5 g) in acetone (1.7 liter) was added p-toluenesulfonic acid mono-hydrate (1.0 g) and the resulting solution stirred for 28 h. The solvents were evaporated; and the residue was dissolved in ether, washed (saturated NaHCO₃ (3 times), brine)), dried (MgSO₄) and evaporated to afford the aldehyde (20.6 g): TLC, $R_f=0.48$, methanol:chloroform (5:95): MS, m/e=236(M+1), 192, 91.

f.
(3S)-3-(Benzyloxycarbonyl)amino-2-hydroxy-4-methylpentanenitrile (Formula XIIIa, W=CN)

A 500 ml round bottomed flask with stirrer was dried under vacuum and purged with nitrogen. The flask was charged with methylene chloride (265 ml) followed by the addition of the aldehyde product of Example 19e (20.6 g) and triethyl amine (7.40 ml). Acetone cyanohydrin (24.0 ml) was added in one portion. The reaction mixture was stirred for 6 h and the solvent evaporated. The crude product was dissolved in ether, washed (water (3 times), brine), dried (MgSO₄), and evaporated. The resulting crude oil was flash chromatographed, eluting with methylene chloride:methanol:NH40H (99:1:0.1) to afford the cyanohydrin (18.0 g, 78%) as a yellow solid: TLC, $R_f=0.53$, acetone:hexanes (50:50).

g.
(2S)-2-[2-(Benzyloxycarbonyl)amino-1-hydroxy-3-methylbutyl]benzoxazole-5-carboxamide (Formula XIVa, heterocycle containing X, N and Q=5-(aminocarbonyl)benzoxazol-2-yl)

A 1 liter flask with stirrer was dried under vacuum and purged with nitrogen. The flask was charged with freshly distilled acetyl chloride (98.0 ml) and chloroform (100 ml) and cooled in an ice bath. Ethanol (89.0 ml) was added dropwise over 45 min maintaining the temperature below 15°. After cooling to 5°, a solution of the product of Example 19f (12.0 g) in chloroform (100 ml) was added dropwise over the course of 10 min. The reaction mixture was allowed to stir for 2 h in an ice bath and the solvent evaporated at 0° to afford a tan foam (14.1 g, 100%): TLC, after partitioning an aliquot between ethyl acetate and saturated NaHCO₃ to form the free imino ether, $R_4=0.40$, acetone:hexanes (50:50); MS, m/e=309(M+1). This foam was dissolved in absolute ethanol (230 ml) and 3-amino-4-hydroxybenzamide (7.30 g) was added. The mixture was refluxed for 1.5 h and the solvent evaporated to afford a brown solid. The solid residue was dissolved in 500 ml ethyl acetate, washed (1N HCl saturated with NaCl, saturated NaHCO₃/NaCl, brine), dried (MgSO₄), and evaporated. This residue was dissolved in methanol, adsorbed onto diatomaceous earth, and flash chromatographed, eluting with acetone:hexanes (50:50), to afford the alcohol (7.15 g, 39%) as a tan solid: TLC, $R_f=0.11$, acetone:hexanes (50:50); MS, m/e=290, 246.

h.
(2S)-2-(2-Amino-1-hydroxy-3-methylbutyl)benzoxazol-5-carboxamide (Formula XVa, heterocycle containing X, N and Q=5-(aminocarbonyl)benzoxazol-2-yl)

A mixture of 10% (w/w) palladium on carbon (1.26 g, 50% (w/w) water wet) and the product from Example 19g (5.00 g), in ethanol (63 ml) was hydrogenated in a shaker at 3.4 bar for 18 h. The mixture was filtered through diatomaceous earth and the solvent evaporated to afford the amine (3.13 g, 95%) as a tan solid: TLC, $R_f=0.20$, methylene chloride:methanol:NH₄OH (95:5:0.5): MS, m/e=264 (M+1).

i.
(1S)-[4-[(4-Chlorophenyl)sulfonylaminocarbonyl]benzoyl]-L-valyl-N-[1-[5-(aminocarbonyl)benzoxazol-2-yl]hydroxymethyl-2-methylpropyl]-L-prolinamide (Formula III, heterocycle containing X, N and Q=5-(aminocarbonyl)benzoxazol-2-yl, A=CO, L=p-phenylene, $R^4=R^5.S(O_2).NH.CO-$, $R^5=4-ClC_6H_4$)

1-(3-Dimethylaminopropyl)-3-ethylcarbodiimide hydrochloride (1.57 g) was added to a solution of the product of Example 19h (1.57 g), 1-hydroxybenztriazole (1.01 g) and the acid product of Example 19d (4.00 g) in dimethylformamide (75 ml) and the solution stirred at room temperature for 60 h. The solvent was evaporated and the brown oil washed with 1N HCl saturated with NaCl, forming a tan precipitate. After the precipitate was filtered and a portion of the solid (750 mg) was removed, the crude precipitate was dissolved in methanol, adsorbed onto diatomaceous earth and purified by flash chromatography, eluting with methylene chloride:methanol:NH₄OH (gradient 85:15:1 to 70:30:1), to afford the alcohol (3.58 g, 59%) as a tan solid: TLC, $R_f=0.22$, methylene chloride:methanol:acetic acid (90:10:0.2): MS, m/e=421.

j.
(S)-[4-[(4-Chlorophenyl)sulfonylaminocarbonyl]benzoyl]-L-valyl-N-[1-[5-(aminocarbonyl)benzoxazol-2-yl)carbonyl-2-methylpropyl]-L-prolinamide (Formula I, heterocycle containing X, N and Q=5-(aminocarbonyl)benzoxazol-2-yl, A=CO, L=p-phenylene, $R^4=R^5.S(O_2).NH.CO-$, $R^5=4-ClC_6H_4$)

To a solution of alcohol prepared in a similar manner to that described in Example 19i, above, (50 mg) and 1-(3-dimethylaminopropyl)-3-ethylcarbodiimide hydrochloride (183 mg) in dimethylsulphoxide (1.0 ml) and toluene (1.0 ml) was added dichloroacetic acid (8.2 mg, 0.0052 ml). The mixture was allowed to stir for 16 h, then additional dichloroacetic acid (0.011 ml) was added and stirring continued for an additional 24 h. The reaction mixture was dissolved in chloroform, washed (1N HCl, brine), dried (MgSO₄), and the solvents evaporated to afford the title compound (42 mg).

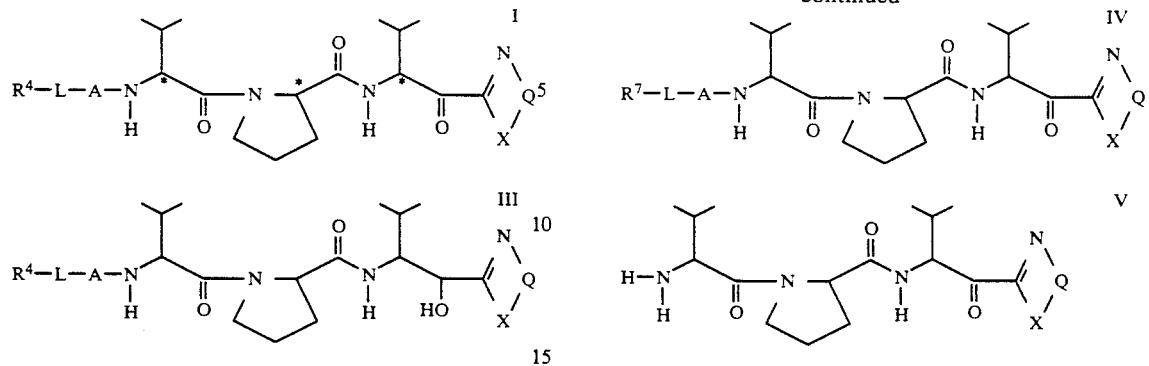
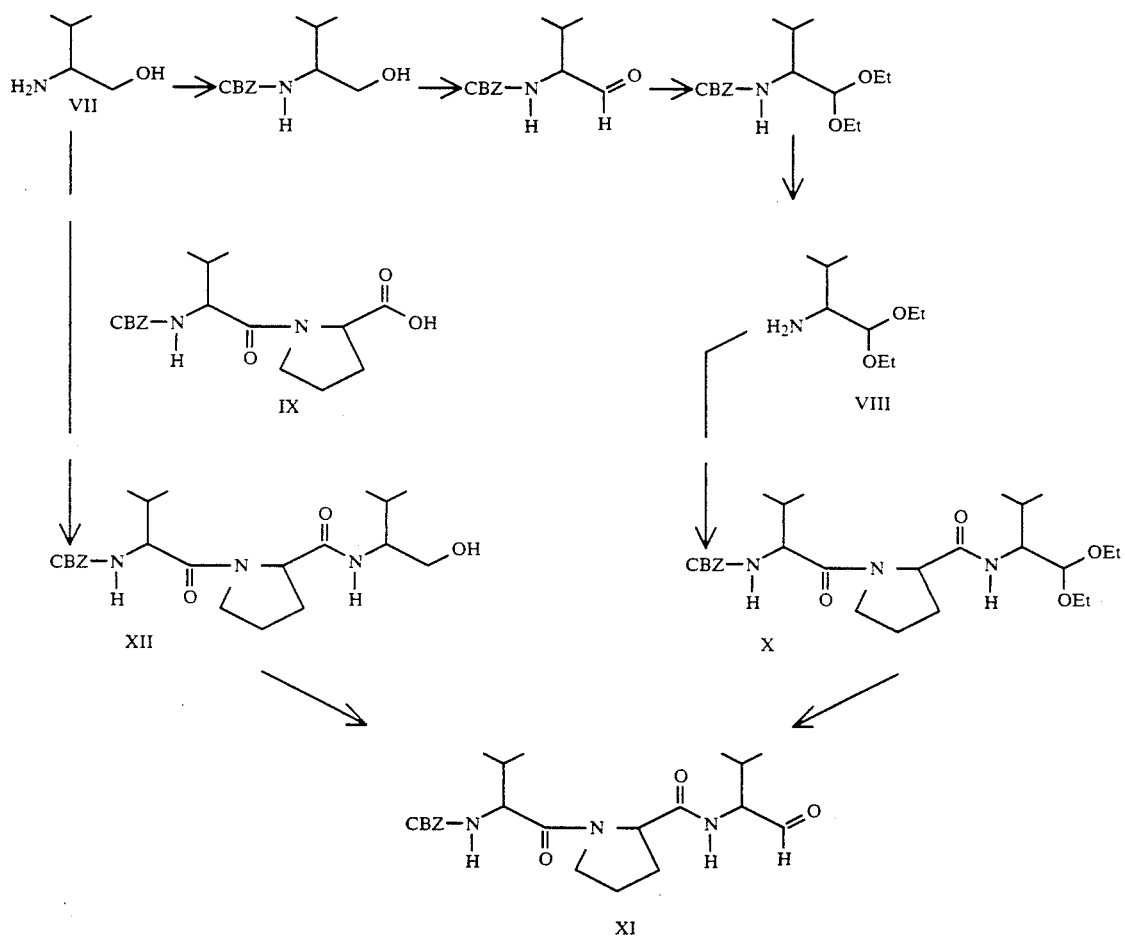
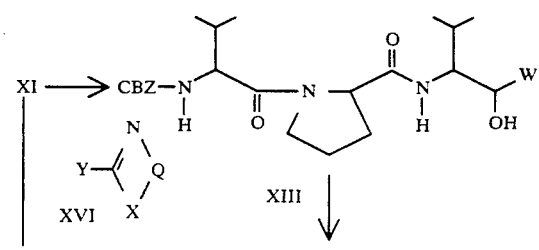

5,164,371
-continued
Scheme II
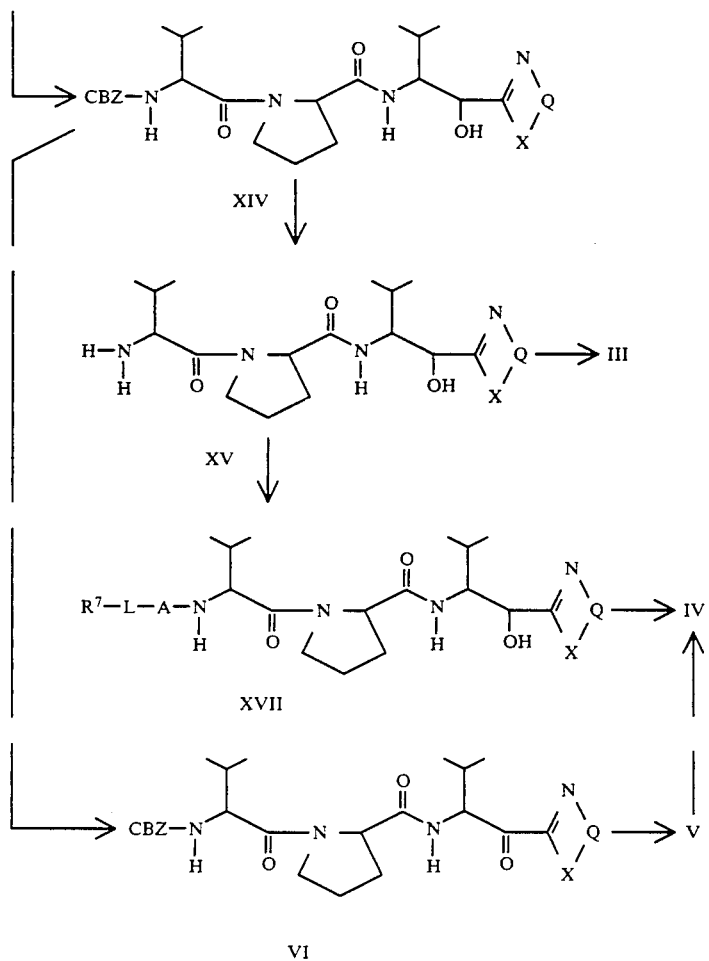
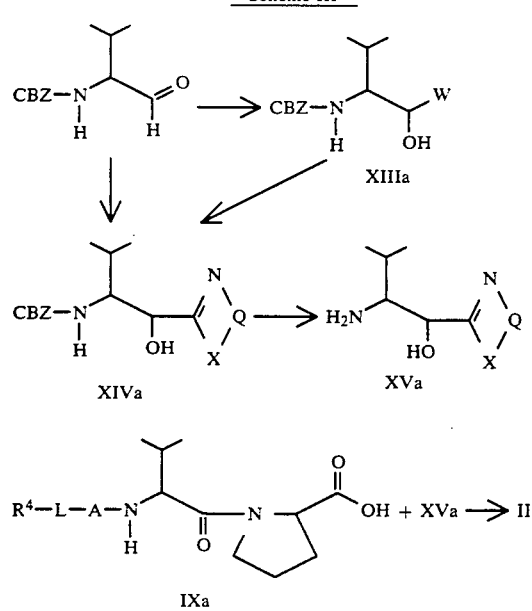
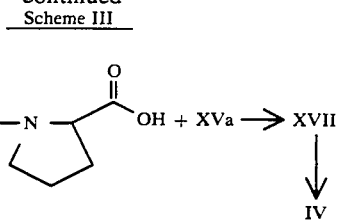
-continued
Scheme III
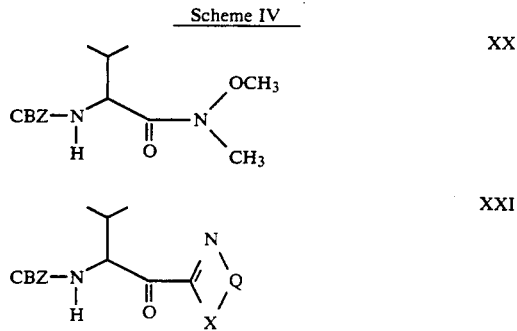

-continued
Scheme IV

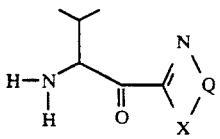
XXII

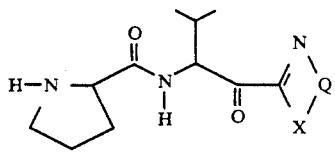
XXIII

What is claimed is:
1. A compound of formula I:

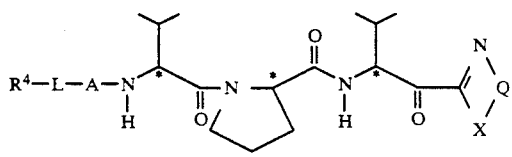
I wherein
  the group —Q— is selected from a group consisting of (i) ortho-phenylene, optionally bearing one or two substituents independently selected from a group consisting of halogeno, nitro, an amino group of formula —$NR^gR^h$, an acylamino group of formula —$NHCOR^m$, hydroxy, an acyloxy group of formula —$OCOR^n$, (1–4C)alkoxy, (1–4C)alkyl, trifluoromethyl, carboxy, cyano, {(1–4C)alkoxy}carbonyl, an aminocarbonyl group of formula —$CONR^pR^q$ (including formula —$CONR_2^p$ when $R^p=R^1$), sulfo, sulfonamido of formula $SO_2NR^iR^j$ and (1–3C)hydroxyalkyl; and (ii) a cis-vinylene group of formula —$C(R^a)=C(R^b)$— wherein
  $R^a$ and $R^b$ are each independently selected from a group consisting of hydrogen, nitro, an amino group of formula —$NR^gR^h$, an acyloxy group of formula —$OCOR^n$, (1–4C)alkoxy, (1–6C)alkyl, trifluoromethyl, carboxy, cyano, {(1–4C)alkoxy}carbonyl, an aminocarbonyl group of formula —$CONR^pR^q$ (including formula —$CONR_2^p$ when $R^p=R^1$), sulfo, sulfonamido of and phenyl optionally bearing one or two substituents chosen from a group consisting of halogeno, nitro, (1–4C)alkoxy, (1–4C)alkyl and trifluoromethyl;
  $R^g$, $R^h$, $R^i$, $R^j$, $R^m$, $R^p$ and $R^q$ are each independently selected from a group consisting of hydrogen and (1–4C)alkyl;
  $R^n$ is (1–4C)alkyl;
  X is selected from a group consisting of oxygen and sulfur,
  A is selected from a group consisting of —CO—, —NH.CO— and —O.CO—;
  L is selected from a group consisting of phenylene, (1–6C)alkanediyl, (2–6C)alkenediyl and phenylene(1–3C)alkyl optionally containing one double bond in the alkyl portion, provided that a carbon included in a double bond of an alkenediyl or included in an optional double bond of a phenylenealkyl group is not directly bonded to an oxygen or nitrogen atom of group A; and
  $R^4$ is selected from a group consisting of an acylsulfonamide of formula $R^5.S(O_2).NH.CO$—, an acylsulfonamide of formula $R^5.CO.NH.S(O_2)$—, a sulfonylurea of formula $R^5.NH.CO.NH.S(O_2)$—, a sulfonylurea of formula $R^5.S(O_2).NH.CO.NR^6$—, and a trifluoromethylsulfonamide of formula $CF_3.S(O_2).NH$—
  wherein
    $R^5$ is selected from a group consisting of (1–10C)alkyl, trifluoromethyl, (3–10C)cycloalkyl, (6 and 10C)aryl optionally substituted by 1 to 3 members of a group consisting of halogeno, nitro, amino, dimethylamino, hydroxy, methyl, trifluoromethyl, carboxy, phenyl, and {(1–5C)alkylcarbonyl}amino; and an aromatic heterocyclic group selected from the group consisting of furyl, thienyl, pyridyl and pyrimidinyl in which up to 3 carbons of the aromatic system may bear a substituent group independently selected from a group consisting of halogeno and trifluoromethyl; and
    $R^6$ is hydrogen or methyl; or
  a pharmaceutically acceptable base-addition salt thereof.
2. A compound as claimed in claim 1 wherein an optional substituent on Q when Q is orthophenylene is selected from a group consisting of fluoro, chloro, bromo, nitro, an amino group of formula $NR^gR^h$, an acylamino group of formula —$NHCOR^m$, hydroxy, an acyloxy group of formula —$OCOR^n$, methoxy, ethoxy, propoxy, isopropoxy, t-butoxy, methyl, ethyl, propyl, isopropyl, 2-methylpropyl, t-butyl, trifluoromethyl, carboxy, cyano, methoxycarbonyl, ethoxycarbonyl, t-butoxycarbonyl, an aminocarbonyl group of formula —$CONR^pR^q$, sulfo, sulfonamido of formula $SO_2NR^iR^j$, hydroxymethyl, 2-hydroxyethyl, and 1,1-dimethylhydroxymethyl, wherein $R^g$, $R^h$, $R^i$, $R^j$, $R^m$, $R^p$ and $R^q$ are each independently selected from a group consisting of hydrogen, methyl, ethyl, propyl, isopropyl, 2-methylpropyl and t-butyl, and $R^n$ is selected from a group consisting of methyl, ethyl, propyl, isopropyl, 2-methylpropyl and t-butyl; $R^a$ and $R^b$ are each independently selected from a group consisting of hydrogen, nitro, an amino group of formula —$NR^gR^h$, an acyloxy group of formula —$OCOR^n$, methoxy, ethoxy, propoxy, isopropoxy, t-butoxy, methyl, ethyl, propyl, isopropyl, butyl, 2-methylpropyl, t-butyl, trifluoromethyl, carboxy, cyano, methoxycarbonyl, ethoxycarbonyl, t-butoxycarbonyl, an aminocarbonyl group of formula $CONR^pR^q$, hydroxymethyl, and phenyl wherein the phenyl optionally bears one or two substituents chosen from a group consisting of fluoro, chloro, bromo, nitro, methoxy, ethoxy, propoxy, isopropoxy, t-butoxy, methyl, ethyl, propyl, isopropyl, 2-methylpropyl, t-butyl and trifluoromethyl, wherein $R^g$, $R^h$, $R^p$ and $R^q$ are each independently selected from a group consisting of hydrogen, methyl, ethyl, propyl, isopropyl, 2-methylpropyl and t-butyl, and $R^n$ is methyl, ethyl, propyl, isopropyl, 2-methylpropyl or t-butyl;
  $R^5$ is selected from a group consisting of methyl, ethyl, propyl, isopropyl, t-butyl, 4-methylpentyl, trifluoromethyl, cyclopropyl, cyclopentyl, cyclohexyl, norbornyl, adamantyl, phenyl, naphthyl (in which an optional substituent on the phenyl or naphthyl is fluoro chloro, bromo, nitro, amino, dimethylamino, hydroxy, methyl, trifluoromethyl, carboxy, phenyl, formylamino, acetylamino, 2-methylpropanoylamino or 2,2-dimethylpropanoylamino), furyl, thienyl, pyridyl and pyrimidinyl optionally substituted on the aromatic heterocyclic group by fluoro, chloro, bromo or trifluoromethyl: and L is selected from a group consisting of p-phenylene, m-phenylene, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl, pentan-1,5-diyl, ethen-1,2-diyl, propen-1,2-diyl, propen-1,3-diyl, buten-1,4-diyl, but-2-en-1,4-diyl, penten-1,5-diyl, 3,3-dimethylpropen-1,3-diyl, p-phenylenemethyl, 2-(p-phenylene)ethyl, 2-(p-phenylene)-2-propyl, and 2-(p-phenylene)ethenyl.

3. A compound as claimed in claim 2 wherein an optional substituent on Q when Q is o-phenylene is chloro, dimethylamino, acetylamino, hydroxy, acetoxy, methoxy, methyl, trifluoromethyl, carboxy, cyano, methoxycarbonyl, ethoxycarbonyl, aminocarbonyl, methylaminocarbonyl, dimethylaminocarbonyl, aminosulfonyl, dimethylaminosulfonyl or hydroxymethyl;

$R^a$ and $R^b$ are each independently selected from a group consisting of hydrogen, dimethylamino, acetoxy, methoxy, methyl, trifluoromethyl, cyano, methoxycarbonyl, aminocarbonyl, methylaminocarbonyl, dimethylaminocarbonyl, hydroxymethyl, phenyl, chlorophenyl, methoxyphenyl and trifluoromethylphenyl;

$R^4$ is $R^5.S(O_2).NH.CO-$, $R^5.S(O_2).NH.CO.NR^6-$, or $CF_3SO_2NH-$;

$R^5$ is selected from a group consisting of methyl, ethyl, isopropyl, cyclopropyl, cyclopentyl, phenyl, chlorophenyl, bromophenyl, trifluoromethylphenyl, 1-naphthyl, 2-thienyl, 2-pyridyl and chloropyridyl;

$R^6$ is hydrogen;

A is —CO—: and

L is p-phenylene, ethane-1,2-diyl, ethen-1,2-diyl, p-phenylenemethyl or 2-(p-phenylene)ethenyl.

4. A compound as claimed in claim 3 wherein an optional substituent on Q is hydroxy, methoxy, carboxy, methoxycarbonyl, aminocarbonyl or hydroxymethyl:

$R^a$ and $R^b$ are hydrogen;

$R^5$ is methyl, isopropyl, phenyl or 4-chlorophenyl: and

L is p-phenylene.

5. A compound as claimed in claim 1 selected from a group consisting of a benzoxazole wherein X is oxygen and Q is ortho-phenylene, an oxazole wherein X is oxygen and Q is a cis-vinylene group of formula —C(-$R^a$)=C($R^b$)—, a benzothiazole wherein X is sulfur and Q is ortho-phenylene, and a thiazole wherein X is sulfur and Q is a cis-vinylene group of formula —C($R^a$)=C($R^b$)— and wherein an ortho-phenylene group may optionally bear one or two substituents independently selected from a group consisting of halogeno, nitro, an amino group of formula —$NR^gR^h$, hydroxy, acetoxy, (1–4C)alkoxy, (1–4C)alkyl, trifluoromethyl, carboxy, [(1–4C)alkoxy]carbonyl, sulfo and sulfonamido of formula $SO_2NR^iR^j$; and wherein $R^a$ and $R^b$ are each independently selected from a group consisting of hydrogen, nitro, an amino group of formula —$NR^gR^h$, (1–4C)alkoxy, (1–6C)alkyl, trifluoromethyl, carboxy, cyano, [(1–4C)alkoxy]carbonyl, and phenyl optionally bearing one or two substituents chosen from a group consisting of halogeno, nitro, (1–4C)alkoxy, (1–4C)alkyl and trifluoromethyl;

$R^g$, $R^h$, $R^i$ and $R^j$ are each independently selected from a group consisting of hydrogen and (1–4C)alkyl;

A is selected from a group consisting of —CO—, —NH.CO— and —O.CO—;

L is selected from a group consisting of phenylene, (1–6C)alkanediyl, (2–6C)alkenediyl and phenylene(1–3C)alkyl, optionally containing one double bond in the alkyl portion, provided that a double bond of an alkenediyl or an optional double bond of a phenylenealkyl group is not directly bonded to an oxygen or nitrogen atom of group A; and $R^4$ is selected from a group consisting of acylsulfonamide of formula $R^5.S(O_2).NH.CO-$, acylsulfonamide of formula $R^5.CO.NH.S(O_2)-$, sulfonylurea of formula $R^5.NH.CO.NH.S(O_2)-$ and sulfonylurea of formula $R^5.S(O_2).NH.CO.NR^6$; or a pharmaceutically acceptable base-addition salt thereof.

6. A compound as claimed in claim 1 selected from a group consisting of:

(a) a benzoxazole wherein X is oxygen and Q is o-phenylene as defined under (i) in the definition of Q;

(b) an oxazole wherein X is oxygen and Q is cis-vinylene as defined under (ii) in the definition of Q;

(c) a benzothiazole wherein X is sulfur and Q is o-phenylene as defined under (i) in the definition of Q; and (d) a thiazole wherein X is sulfur and Q is cis-vinylene as defined under (ii) in the definition of Q, and pharmaceutically acceptable base-addition salts thereof.

7. A compound as claimed in any one of claims 1, 2, 3, 5 or 6 wherein X is oxygen; $R^4$ is $R^5.S(O_2).NH.CO-$ or $R^5.S(O_2).NH.CO.NR^6-$; L is p-phenylene; A is —CO—; and $R^5$ is 4-chlorophenyl.

8. A compound as claimed in claim 4 wherein X is oxygen $R^4$ is $R^5.S(O_2).NH.CO-$; L is p-phenylene: A is —CO—; and $R^5$ is 4-chlorophenyl.

9. A compound as claimed in claim 1 selected from a group consisting of:

(i) [4-[(4-chlorophenyl)sulfonylaminocarbonyl]benzoyl]-L-valyl-N-[1-(5-hydroxybenzoxazol-2-yl)carbonyl-2-methylpropyl]-L-prolinamide;

(ii) [4-[(4-chlorophenyl)sulfonylaminocarbonyl]benzoyl]-L-valyl-N-[1-[5-(aminocarbonyl)benzoxazol-2-yl)carbonyl-2-methylpropyl]-L-prolinamide;

(iii) [4-[(4-chlorophenyl)sulfonylaminocarbonyl]benzoyl]-L-valyl-N-[1-[5-(hydroxymethyl)benzoxazol-2-yl]carbonyl-2-methylpropyl]-L-prolinamide;

and pharmaceutically acceptable base-addition salts thereof.

10. A salt as claimed in claim 1 wherein said salt is made with a base forming a physiologically acceptable cation.

11. A pharmaceutical composition comprising a compound of claim 1 or a pharmaceutically acceptable base-addition salt thereof in an amount sufficient to inhibit human leukocytic elastase and a pharmaceutically acceptable diluent or carrier.

12. A method of treating emphysema in a mammal comprising administering to the mammal a pharmacologically effective amount of a compound of claim 1.

13. A composition as claimed in claim 11 wherein said composition is in the form of a liquid or powdered aerosol.

* * * * *